United States Patent [19]
Chari et al.

[11] Patent Number: 5,416,064
[45] Date of Patent: May 16, 1995

[54] CYTOTOXIC AGENTS COMPRISING MAYTANSINOIDS AND THEIR THERAPEUTIC USE

[75] Inventors: Ravi J. Chari, Boston; Victor S. Goldmacher, Newton Center; John M. Lambert, Cambridge; Walter A. Blattler, Brookline, all of Mass.

[73] Assignee: ImmunoGen, Inc., Cambridge, Mass.

[21] Appl. No.: 986,578

[22] Filed: Dec. 7, 1992

Related U.S. Application Data

[63] Continuation of Ser. No. 911,380, Jul. 13, 1992, Pat. No. 5,208,020, which is a continuation of Ser. No. 426,247, Oct. 25, 1989, abandoned.

[51] Int. Cl.$^6$ .................. C07D 491/12; A61K 31/645
[52] U.S. Cl. .................................. 514/229.5; 540/462
[58] Field of Search ...................... 540/462; 514/229.5

[56] References Cited

U.S. PATENT DOCUMENTS

| | | | |
|---|---|---|---|
| 3,896,111 | 7/1975 | Kupchan | 540/462 |
| 4,137,230 | 1/1979 | Hashimoto | 540/462 |
| 4,248,870 | 2/1981 | Miyashita | 514/229.5 |
| 4,256,746 | 3/1981 | Miyashita | 514/229.5 |
| 4,260,608 | 4/1981 | Miyashita | 514/229.5 |
| 4,263,294 | 4/1981 | Miyashita | 514/229.5 |
| 4,264,596 | 4/1981 | Miyashita | 514/229.5 |
| 4,294,757 | 10/1981 | Asai | 540/462 |
| 4,307,016 | 12/1981 | Asai | 540/462 |
| 4,308,268 | 12/1981 | Miyashita | 514/229.5 |
| 4,308,269 | 12/1981 | Miyashita | 514/229.5 |
| 4,309,428 | 1/1982 | Miyashita | 514/229.5 |
| 4,313,946 | 2/1982 | Powell | 514/229.5 |
| 4,362,663 | 12/1982 | Kida | 540/462 |
| 4,364,866 | 12/1982 | Asai | 540/462 |
| 4,418,064 | 11/1983 | Powell | 514/229.5 |
| 4,424,219 | 1/1984 | Hashimoto | 514/229.5 |

FOREIGN PATENT DOCUMENTS 0205326 12/1986 European Pat. Off. ...... C07C 17/08
0376176 12/1989 European Pat. Off. ...... C12P 21/08

OTHER PUBLICATIONS

Chari et al., "Immunoconjugates Containing Novel Maytansinoids: Promising Anticancer Drugs", Cancer Research, vol. 52, (Jan. 1, 1992), pp. 127–131.
Kupchan et al., "Structural Requirements for Antileukemic Activity Among the Naturally Occurring and Semisynthetic Maytansinoids", Journal of Medicinal Chemistry, vol. 21, No. 1, (1978), pp. 31–37.
Kawai et al., "Chemical Modification of Ansamitochins. III. Synthesis and Biological Effects of 3-Acyl Esters of Maytansinol", Chem. Pharm. Bull., vol. 32, No. 9, (1984), pp. 3441–3451.

Primary Examiner—Howard T. Mars
Assistant Examiner—Michael B. Hydorn
Attorney, Agent, or Firm—Sughrue, Mion, Zinn, Macpeak & Seas

[57] ABSTRACT

A cytotoxic agent comprising one or more maytansinoids linked to a cell binding agent. A therapeutic agent for killing selected cell populations comprising: (a) a cytotoxic amount of one or more maytansinoids linked to a cell binding agent, and (b) a pharmaceutically acceptable carrier, diluent or excipient. A method for killing selected cell populations comprising contacting a cell population or tissue suspected of containing cells from said selected cell population with a cytotoxic amount of a cytotoxic agent comprising one or more maytansinoids linked to a cell binding agent. An N-methyl-alanine-containing ester of maytansinol or an analogue of maytansinol, said N-methyl-alanine-containing ester comprising a linking group capable of linking an N-methyl-alanine-containing maytansinoid ester to a chemical moiety. N-methyl-cysteine-containing ester of maytansinol or an analogue of maytansinol.

20 Claims, 4 Drawing Sheets

1a COCH(CH₃)N(CH₃)COCH₃
1b H

CYTOTOXIC AGENTS COMPRISING MAYTANSINOIDS AND THEIR THERAPEUTIC USE

This is a continuation of application Ser. No. 07/911,380 filed Jul. 13, 1992, now U.S. Pat. No. 5,208,020, which is a Continuation of Ser. No. 07/426,247, filed Oct. 25, 1989, (now abandoned).

FIELD OF THE INVENTION

The present invention relates to novel cytotoxic agents and their therapeutic use. More specifically, the invention relates to novel cytotoxic agents comprising maytansinoids and their therapeutic use. These novel cytotoxic agents have therapeutic use as a result of delivering the maytansinoids to a specific cell population in a targeted fashion by chemically linking the maytansinoid to a cell binding agent.

BACKGROUND OF THE INVENTION

In recent years, a myriad of reports have appeared on the attempted specific targeting of tumor cells with monoclonal antibody-drug conjugates (Sela et al, in *Immunoconjugates* 189–216 (C. Vogel, ed. 1987); Ghose et al, in *Targeted Drugs* 1–22 (E. Goldberg, ed. 1983); Diener et al, in *Antibody mediated delivery systems* 1–23 (J. Rodwell, ed. 1988); Pietersz et al, in *Antibody mediated delivery systems* 25–53 (J. Rodwell, ed. 1988); Bumol et al, in *Antibody mediated delivery systems* 55–79 (J. Rodwell, ed. 1988). Cytotoxic drugs such as methotrexate, daunorubicin, doxorubicin, vincristine, vinblastins, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, 46 *Cancer Res.* 2407–2412 (1986); Ohkawa et al 23 *Cancer Immunol. Immunother.* 81–86 (1986); Endo et al, 47 *Cancer Res.* 1076–1080 (1980)), dextran (Hurwitz et al, 2 *Appl. Biochem.* 25–35 (1980); Manabi et al, 34 *Biochem. Pharmacol.* 289–291 (1985); Dillman et al, 46 *Cancer Res.* 4886–4891 (1986); Shovel et al, 85 *Proc. Natl. Acad. Sci.* 8276–8280 (1988)), or polyglutamic acid (Tsukada et al, 73 *J. Natl. Canc. Inst.* 721–729 (1984); Kato et al 27 *J. Med. Chem.* 1602–1607 (1984); Tsukada et al, 52 *Br. J. Cancer* 111–116 (1985)).

A wide array of linker technologies have been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (102 *Biochem. Biophys. Res. Commun.* 1048–1054 (1981)). Yang and Reisfeld used the same technique to conjugate daunorubicin to an anti-melanoma antibody (80 *J. Natl. Canc. Inst.* 1154–1159 (1988)). Recently, Dillman et al also used an acid-labile linker in a similar fashion to prepare conjugates of daunorubicin with an anti-T cell antibody (48 *Cancer Res.* 6097–6102 (1988)).

An alternative approach, explored by Trouet et al, involved linking daunorubicin to an antibody via a peptide spacer arm (79 *Proc. Natl. Acad. Sci.* 626–629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al, 260 *J. Biol. Chem.* 12035–12041 (1985); Lambert et al, in *Immunotoxins* 175–209 (A. Frankel, ed. 1988); Ghetie et al 48 *Cancer Res.* 2610–2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al described the conversion of methotrexate into a mercaptoethylamide derivative followed by conjugation with poly-D-lysine via a disulfide bond (260 *J. Biol. Chem.* 10905–10908 (1985)). A recent report described the preparation of a conjugate of the trisulfide-containing toxic drug calicheamycin with an antibody (Menendez et al, *Fourth International Conference on Monoclonal Antibody Immunoconjugates for Cancer, San Diego*, Abstract 81 (1989)).

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin and vincristine. In order to achieve significant cytotoxicity, linkage of a large number of drug molecules either directly to the antibody or through a polymeric carrier molecule becomes necessary. However such heavily modified antibodies often display impaired binding to the target antigen and fast in vivo clearance from the blood stream.

Maytansinoids are highly cytotoxic drugs. Maytansine was first isolated by Kupchan et al from the east African shrub *Maytenus serrata* and shown to be 100 to 1000 fold more cytotoxic than conventional cancer chemotherapeutic agents like methotrexate, daunorubicin, and vincristine (U.S. Pat. No. 3,896,111). Subsequently it was discovered that some microbes also produce maytansinoids, such as maytansinol and C-3 esters of maytansinol (U.S. Pat. No. 4,151,042). Synthetic C-3 esters of maytansinol and analoguss of maytansinol have also been reported (Kupchan et al, 21 *J. Med. Chem.* 31–37 (1978); Higashide et al, 270 *Nature* 721–722 (1977); Kawai et al, 32 *Chem. Pharm. Bull.* 3441–3451 (1984)). Examples of analoguss of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters can be classified into two groups:

(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and (b) C-3 esters with derivatives of N-methyl-L-alanine (U.S. Pat. Nos. 4,137,230; 4,260,608; and 12 Chem. Pharm. Bull. 3441 (1984)).

Esters of group (b) were found to be much more cytotoxic than esters of group (a).

Maytansine is a mitotic inhibitor. Treatment of L1210 cells in vitro with maytansine has been reported to result in 67% of the cells accumulating in mitosis. Untreated control cells were reported to demonstrate a mitotic index ranging from between 3.2 to 5.8% (Sieber et al, 43 Comparative Leukemia Research 1975, Bibl. Haemat. 495–500 (1976)). Experiments with sea urchin eggs and clam eggs have suggested that maytansine inhibits mitosis by interfering with the formation of microtubules through the inhibition of the polymerization of the microtubule protein, tubulin (Remillard et al, 189 Science 1002–1005 (1975)).

In vitro P388, L1210, and LY5178 murine leukemic cell suspensions have been found to be inhibited by maytansine at doses of $10^{-3}$ to $10^{-7}$ microgram/ml, with the P388 line being the most sensitive. Maytansine has also been shown to be an active inhibitor of in vitro growth of human nasopharyngeal carcinoma cells and the human acute lymphoblastic leukemia line CEM was reported inhibited by concentrations as low as $10^{-7}$ microgram/ml (Wolpert-DeFillippes et al, 24 Biochem. Pharmacol. 1735–1738 (1975)).

In vivo, maytansine has also been shown to be active. Tumor growth in the P388 lymphocytic leukemia system was shown to be inhibited over a 50- to 100-fold dosage range which suggested a high therapeutic index; also significant inhibitory activity could be demonstrated with the L1210 mouse leukemia system, the human Lewis lung carcinoma system and the human B-16 melanocarcinoma system (Kupchan, 33 Ped. Proc. 2288–2295 (1974)).

Because the maytansinoids are highly cytotoxic, they were expected to be of use in the treatment of many diseases such as cancer. This expectation has yet to be realized. Clinical trials with maytansine were not favorable due to a number of side effects (Issel et al, 5 Can. Trtmnt. Rev. 199–207 (1978)). Adverse effects to the central nervous system and gastrointestinal symptoms were responsible for some patients refusing further therapy (Issel at 204), and it appeared that maytansine was associated with peripheral neuropathy that might be cumulative (Issel at 207).

Accordingly, a method of treating diseases with maytansinoids wherein their side effects are reduced without compromising their cytotoxicity is greatly needed.

SUMMARY OF THE INVENTION

Thus, one object of the present invention is to provide maytansinoids in a form that are highly cytotoxic and that can still be effectively used in the treatment of many diseases.

Another object of the present invention is to provide novel maytansinoid esters.

These and other objects have been achieved by providing a cytotoxic agent comprising one or more maytansinoids linked to a cell binding agent.

In a second embodiment, the present invention provides a therapeutic agent for killing selected cell populations comprising:

(a) a cytotoxic amount of one or more maytansinoids linked to a cell binding agent, and (b) a pharmaceutically acceptable carrier, diluent or excipient.

In a third embodiment, the present invention provides a method for killing selected cell populations comprising contacting a cell population or tissue suspected of containing cells from said selected cell population with a cytotoxic amount of a cytotoxic agent comprising one or more maytansinoids linked to a cell binding agent.

In a fourth embodiment, the present invention provides an N-methyl-alanine-containing ester of maytansinol or an analogue of maytansinol, said N-methyl-alanine-containing ester comprising a linking group capable of linking an N-methyl-alanine-containing maytansinoid ester to a chemical moiety.

In a fifth embodiment, the present invention provides an N-methyl-cysteine-containing ester of maytansinol or an analogue of maytansinol.

DETAILED DESCRIPTION OF THE INVENTION

Figure 1:
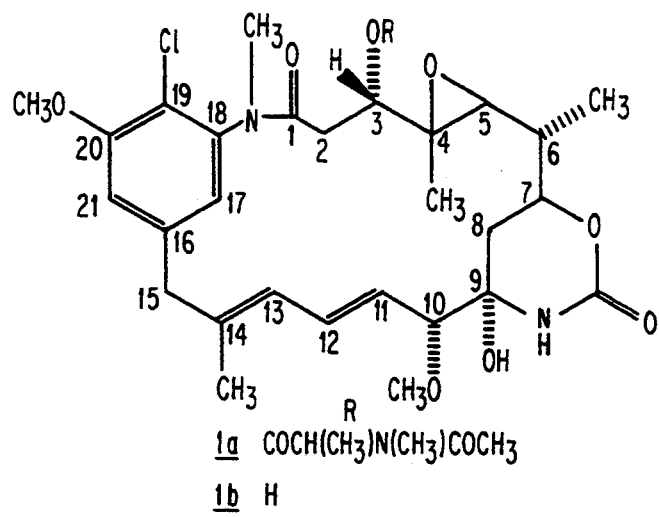
FIG. 1 shows maytansine (1a) and maytansinol (1b).
Figure 2:
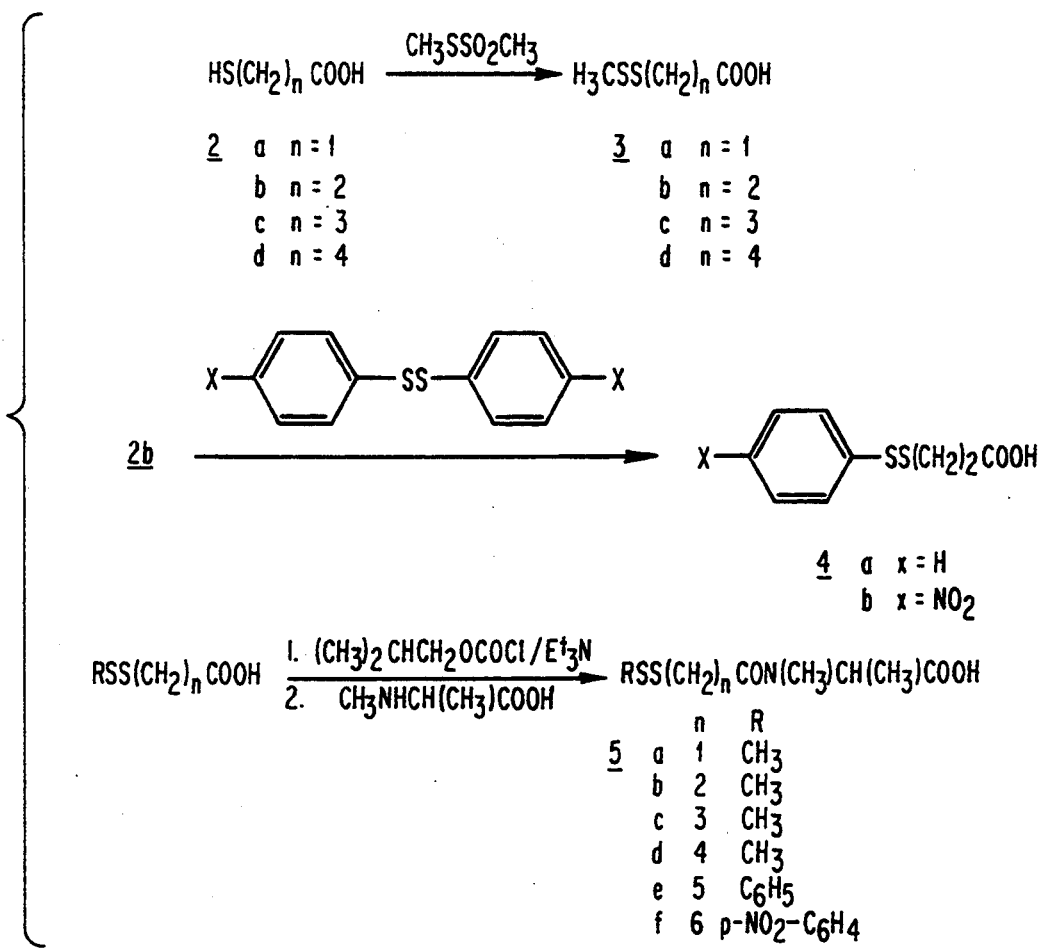
FIG. 2 shows the synthesis of disulfide-containing derivatives of N-methyl-L-alanine.
Figure 3:
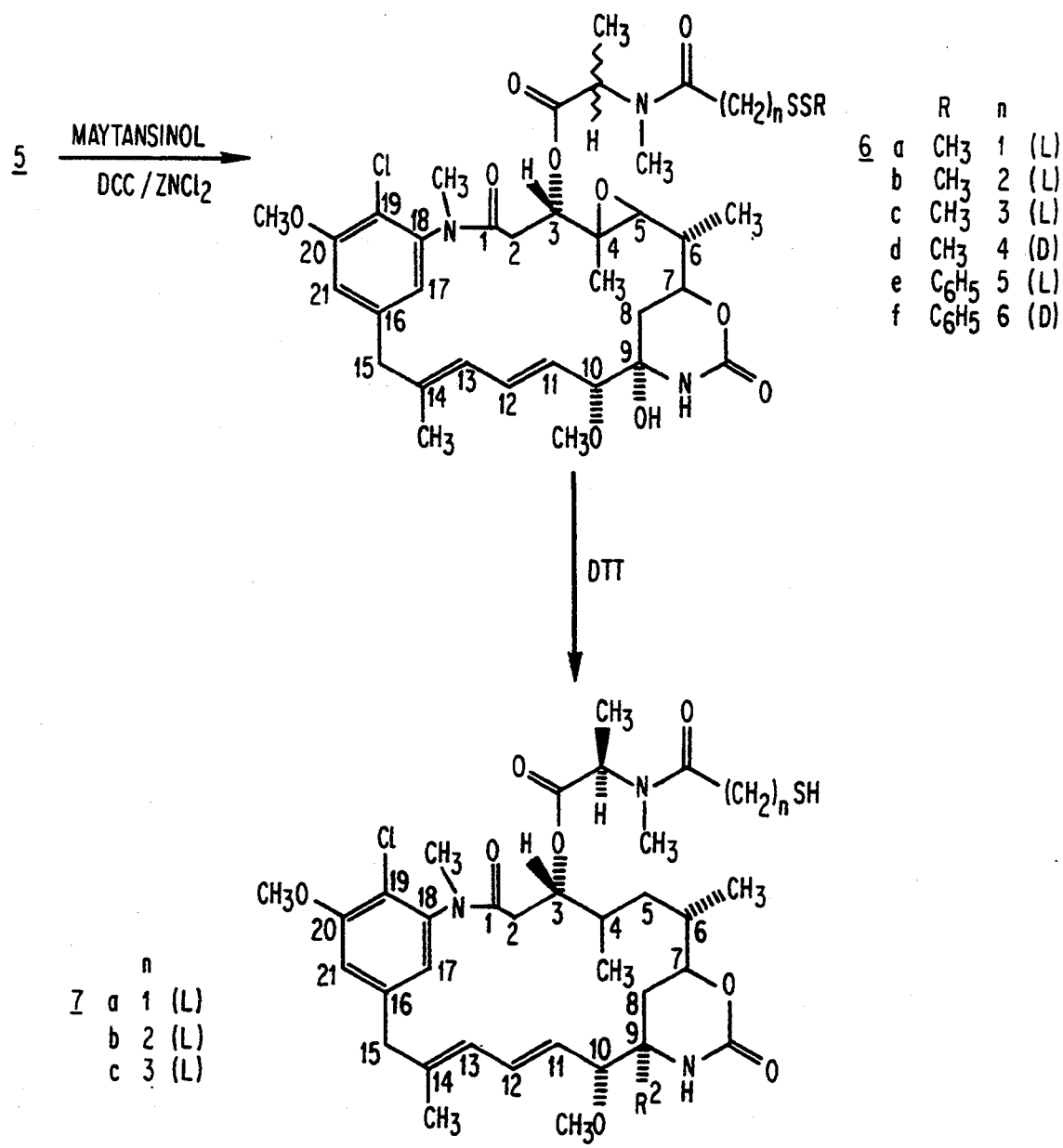
FIG. 3 shows the synthesis of disulfide- and thiol-containing maytansinoids which can be linked to cell binding agents via a disulfide or any other sulfur-containing link such as thioether or thioester links. The synthesis starts with the intermediates of FIG. 2.
Figure 4A:
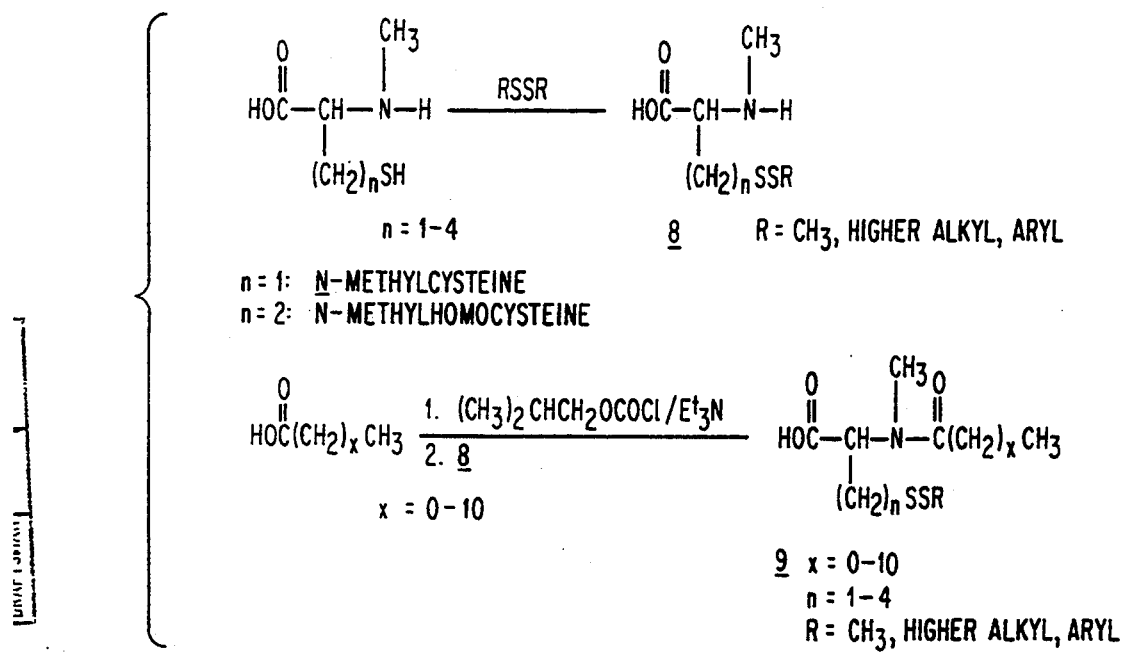
FIG. 4(A) shows the synthesis of disulfide- and thiol-containing derivatives of N-methyl-L-cysteine.
Figure 4B:
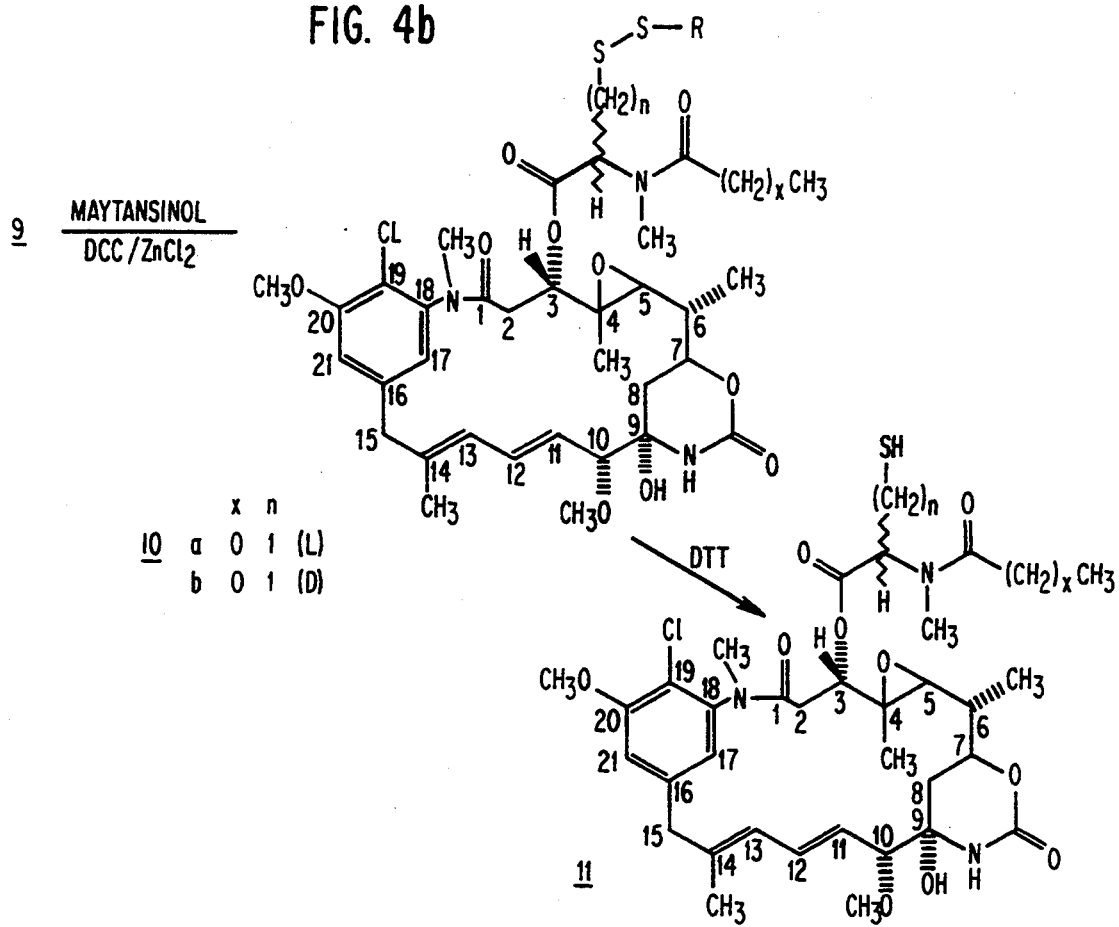
FIG. 4(B) shows the synthesis of disulfide- and thiol-containing maytansinoids from the intermediates of FIG. 4(A) that can be conjugated to cell binding agents via a disulfide or any other sulfur-containing link such as thioether or thioester links.

This invention is based on the synthesis of novel maytansinoid derivatives that retain high cytotoxicity and that can be effectively linked to cell binding agents. The art reveals that it is extremely difficult to modify existing drugs without diminishing their cytotoxic potential. The disclosed invention overcomes this problem by modifying the disclosed maytansinoid derivatives with chemical moieties, especially ones containing thiol or disulfide groups, to which appropriate cell binding agents can be linked. As a result, the disclosed novel maytansinoid derivatives preserve and in some cases even enhance the cytotoxic potency of the naturally occurring maytansinoids. The cell binding agent-maytansinoid derivative conjugates permit the full measure of the cytotoxic action of the maytansinoid derivatives to be applied in a targeted fashion against unwanted cells only, therefore, avoiding side effects due to damage to non-targeted healthy cells. This invention permits the maytansinoid derivatives to live up to their potential, something their undirected cytotoxic effects had previously made impossible. Thus the invention provides useful agents for the elimination of diseased or abnormal cells that are to be killed or lysed such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

Thus, this invention teaches the synthesis of maytansinoid derivatives that can be chemically linked to a cell binding agent while keeping a high cytotoxicity either in bound form or in released form or in both states. High cytotoxicity is defined as exhibiting a toxicity having an $IC_{50}$-the inhibiting concentration of a toxic substance that leaves a surviving fraction of 0.5-of about $10^{-8}M$ or less when measured in vitro with KB cells upon a 24 hour exposure time to the drug.

Cytotoxic Agent

The cytotoxic agent according to the present invention comprises one or more maytansinoids linked to a cell binding agent.

In order to link the maytansinoid to a cell binding agent, the maytansinoid must first be modified.

Maytansinoids that can be used in the present invention to produce the modified maytansinoid capable of being linked to a cell binding agent are well known in the art and can be isolated from natural sources according to known methods or prepared synthetically according to known methods.

Examples of suitable maytansinoids include maytansinol and maytansinol analoguss. Examples of suitable maytansinol analoguss include those having a modified aromatic ring and those having modifications at other positions.

Specific examples of suitable analoguss of maytansinol having a modified aromatic ring include:
(1) C-19-dechloro (U.S. Pat. No. 4,256,746) (prepared by LAH reduction of ansamytocin P2);
(2) C-20-hydroxy (or C-20-demethyl) ±C-19-dechloro (U.S. Pat. Nos. 4,361,650 and 4,307,016) (prepared by demethylation using Streptomyces or Actinomyces or dechlorination using LAH); and
(3) C-20-demethoxy, C-20-acyloxy (—OCOR), ±dechloro (U.S. Pat. No. 4,294,757) (prepared by acylation using acyl chlorides).

Specific examples of suitable analoguss of maytansinol having modifications of other positions include:
(1) C-9-SH (U.S. Pat. No. 4,424,219) (prepared by the reaction of maytansinol with $H_2S$ or $P_2S_5$);
(2) C-14-alkoxymethyl(demethoxy/$CH_2OR$) (U.S. Pat. No. 4,331,598);
(3) C-14-hydroxymethyl or acyloxymethyl ($CH_2OH$ or $CH_2OAc$) (U.S. Pat. No. 4,450,254) (prepared from Nocardia);
(4) C-15-hydroxy/acyloxy (U.S. Pat. No. 4,364,866) (prepared by the conversion of maytansinol by Streptomyces);
(5) C-15-methoxy (U.S. Pat. No. 4,313,946 and 4,315,929) (isolated from *Trewia nudiflora*);
(6) C-18-N-demethyl (U.S. Pat. No. 4,362,663 and 4,322,348) (prepared by the demethylation of maytansinol by Streptomyces); and
(7) 4,5-deoxy (U.S. Pat. No. 4,371,533) (prepared by the titanium trichloride/LAH reduction of maytansinol).

In order to link the maytansinoid to the cell binding agent, a linking group is used.

Suitable linking groups are well known in the art and include disulfide groups, thioether groups, acid labile groups, photolabile groups, peptidase labile groups and esterase labile groups. Preferred are disulfide groups and thioether groups.

According to the present invention the linking group is part of a chemical moiety that is covalently bound to the maytansinoid through conventional methods. In a preferred embodiment, the chemical moiety can be covalently bound to the maytansinoid via. an ester linkage.

Many positions on maytansinoids are expected to be useful as the linkage position, depending upon the type of link. For example, for forming an ester linkage, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

Also preferred is an N-methyl-alanine-containing C-3 ester and an N-methyl-cysteine-containing C-3 ester of maytansinol or its analogues.

Synthesis of Esters of Maytansinol Having a Linking Group

While the synthesis of esters of maytansinol having a linking group is described below in terms of thiol and disulfide linking groups, one of skill in the art will understand that other linking groups, specific representative examples of which are set forth in Example 4, can also be used with the present invention as can other maytansinoids.

The synthesis of maytansinoid derivatives can be described by reference to FIGS. 1, 2, 3, 4(A) and 4(B), where disulfide-containing maytansinoid esters are prepared by condensing maytansinol 1b with freshly prepared N-methyl-L-alanine or N-methyl-L-cysteine derivatives containing a disulfide group.

ω-Mercapto-carboxylic acids of varying chain lengths are converted into their respective methyldithio, e.g. 3a to 3d (where n=1–10, including branched and cyclic aliphatics), or aryl-dithio, e.g. 4a to 4b, derivatives by reacting them with methyl methanethiolsulfonate or aryldisulfides, such as diphenyldisulfide and ring substituted diphenyldisulfides and heterocyclic disulfides such as 2,2'-dithiopyridine. The carboxylic acids are activated and then reacted with N-methyl-L-alanine to form the desired carboxylic acid compounds, e.g. 5a to 5f for condensation with maytansinol 1b.

Esterification of maytansinol 1b or an analogue with the carboxylic acids 5a to 5f gives the disulfide-containing maytansinoids 6a to 6f. Cleavage of the disulfide group in 6a to 6f with dithiothreitol gives the thiol-containing maytansinoids 7a to 7c, which are readily linked via disulfide or thioether links to cell binding agents.

N-methyl-L-alanine can be prepared as described in the literature (See, Fu, S. J. & Birnbaum, S. M., 75 *J. Amer. Chem. Soc.* 918 (1953); or is obtainable commercially (Sigma Chemical Company)).

In another embodiment, N-methyl-cysteine or N-methyl-homocysteine can be converted to the respective disulfide derivatives 8 (n=1 and 2, respectively), which are then acylated to yield the desired carboxylic acids 9 (n=1 and 2, respectively). Maytansinol is then esteriliad with 9 (n=1) to give disulfide-containing ester 10. Reduction of 10a with dithiothreitol as described for 7b produces the thiol-containing maytansinoid 11 which can be conjugated to cell binding agents.

N-methyl-cysteine can be prepared as described in Undheim and Eidem, 23 *Acta Chem. Scand.* 3129-3133 (1970).

More specifically, maytansinol 1b is derived from maytansine 1a or other esters of maytansinol by reduction such as with lithium aluminum hydride. (Kupchan, S. M. et al 21 *J. Med. Chem.* 31-37 (1978); U.S. Pat. No. 4,360,462). It is also possible to isolate maytansinol from the microorganism Nocardia, see, Higashide et al, U.S. Pat. No. 4,151,042 (1979). Maytansinol is then converted to the different ester derivatives, 6a to 6f and 10, using a suitable agent such as dicyclohexylcarbodiimide (DCC) and catalytic Mounts of zinc chloride (See, U.S. Pat. No. 4,137,230; Kawai et al, 32 *Chem. Pharm. Bull.* 3441-3951 (1984); U.S. Pat. No. 4,260,609). The two diastereomeric products containing the D and L-aminoacyl side chains result. The diastereomeric maytansinoid esters are readily separated by preparative TLC on silica gel. For example, using Analtach GF plates (1000 microns) and developing with 6% methanol in chloroform yields distinct banding; the desired bands are scraped off the plate and the products extracted with ethyl acetate. See, Kupchan, S. M., 21 *J. Med. Chem.* 31-37 (1978); and Higashide et al, U.S. Pat. No. 4,360,462 (1982).

Reduction of the disulfide-containing maytansinoids to the corresponding mercapto-maytansinoids 7a, 7b, 7c and 11, is achieved by treatment with dithiothreitol (DTT) and purification by HPLC using a Waters radial-pak C-18 column and eluting with a linear gradient of 55% to 80% acetonitrile in H$_2$O over 10 min. at a flow rate of 1.5 ml/min.

When analogues of maytansinol are used as the starting material to give analogous disulfide-containing maytansinoid esters, the analogues are prepared before reacting them with the N-methyl-L-alanine or N-methyl-L-cysteine derivatives.

Specific examples of N-methyl-alanine-containing maytansinoid derivatives useful in the present invention are represented by the formulae (I), (II), (III) and (IV).

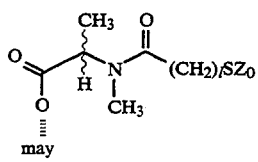
(I)

wherein:
Z$_0$ represents H or SR, wherein R represents methyl, linear alkyl, branched alkyl, cyclic alkyl, simple or substituted aryl or heterocyclic;
l represents an integer of 1 to 10; and
may represents a maytansinoid.

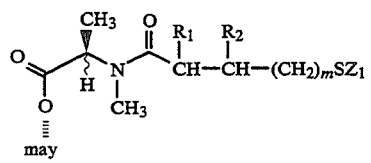
(II)

wherein:
R$_1$ and R$_2$, which may be the same or different, represents H, CH$_3$ or CH$_2$CH$_3$;
Z$_1$ represents H or SR$_3$, wherein R$_3$ represents methyl, linear alkyl, branched alkyl, cyclic alkyl, simple or substituted aryl, or heterocyclic;
m represents 0, 1, 2 or 3; and
may represents a maytansinoid.

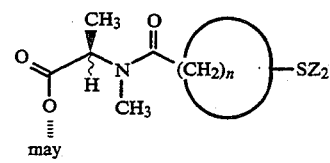
(III)

wherein:
Z$_2$ represents H or SR$_4$, wherein R$_4$ represents methyl, linear alkyl, branched alkyl, cyclic alkyl, simple or substituted aryl, or heterocyclic;
n represents an integer of 3 to 8; and
may represents a maytansinoid.

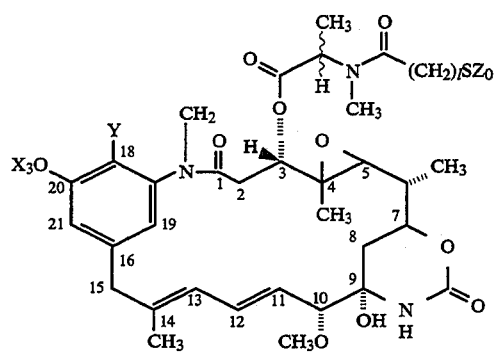
(IV)

wherein:
Z$_0$ represents H or SR, wherein R represents methyl, linear alkyl, branched alkyl, cyclic alkyl, simple or substituted aryl or heterocyclic;
l represents 1, 2 or 3;
y$_0$ represents Cl or H; and
X$_3$ represents H or CH$_3$.

Specific examples of N-methyl-cysteine-containing maytansinoid derivatives useful in the present invention are represented by the formulae (V) and (VI).

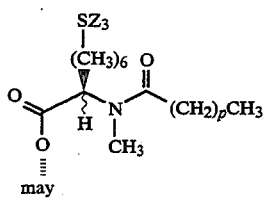
V wherein:

$Z_3$ represents H or $SR_5$, wherein $R_5$ represents methyl, linear alkyl, branched alkyl, cyclic alkyl, simple or substituted aryl, or heterocyclic;

o represents 1, 2 or 3;

p represents 0 or an integer of 1 to 10; and may represents a maytansinoid.

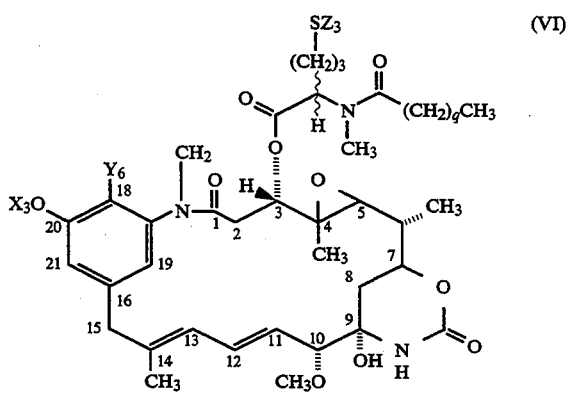

wherein:

$Z_3$ represents H or $S_5$, wherein $R_5$ represents methyl, linear alkyl, branched alkyl, cyclic alkyl, simple or substituted aryl or heterocyclic;

o represents 1, 2, or 3;

q represents 0 or an integer of 1 to 10;

$Y_0$ represents Cl or H; and $X_3$ represents H or $CH_3$.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as Cl, Br, F, nitro groups, amino groups, sulfonic acid groups, carboxylic acid groups, hydroxy groups and alkoxy groups.

Examples of heterocyclics are compounds wherein the heteroatoms are selected from O, N and S, and include pyrrollyl, pyridyl, furyl and thiophene.

Disulfide-containing and mercapto-containing maytansinoid drugs of the invention can be evaluated for their ability to suppress proliferation of various unwanted cell lines in vitro. For example, cell lines such as the human epidermoid carcinoma line KB, the human breast tumor line SKBR3, and the Burkitt's lymphoma line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

Preparation of Cell Binding Agents

The effectiveness of the compounds of the invention as therapeutic agents depends on the careful selection of an appropriate cell binding agent. Cell binding agents may be of any kind presently known, or that become known and include peptides and non-peptides. Generally, these can be antibodies (especially monoclonal antibodies), lymphokines, hormones, growth factors, nutrient-transport molecules (such as transferrin), or any other cell binding molecule or substance.

More specific examples of cell binding agents that can be used include:

monoclonal antibodies;

fragments of antibodies such as Fab, Feb', and F(ab')$_2$ (Parham, 131 *J. Immunol.* 2895–2902 (1983); Spring et al, 113 *J. Immunol.* 470–478 (1974); Nisonoff et al, 89 *Arch. Biochem. Biophys.* 230–244 (1960));

interferons (e.g. $\alpha$, $\beta$, $\gamma$);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-$\alpha$, G-CSF, M-CSF and GM-CSF (Burgess, 5 *Immunology Today* 155–158 (1984)); and transferrin (O'Keefe et al, 260 *J. Biol. Chem.* 932–937 (1985)).

Monoclonal antibody techniques allow for the production of extremely specific cell binding agents in the form of specific monoclonal antibodies. Particularly well known in the art are techniques for creating monoclonal antibodies produced by immunizing mice, rats, hamstars or any other mammal with the antigen of interest such as the intact target cell, antigens isolated from the target cell, whole virus, attenuated whole virus, and vital proteins such as vital coat proteins. Sensitized human cells can also be used.

Selection of the appropriate cell binding agent is a matter of choice that depends upon the particular cell population that is to be targeted, but in general monoclonal antibodies are preferred if an appropriate one is available.

For example, the monoclonal antibody J5 is a murine $IgG_{2a}$ antibody that is specific for the Common Acute Lymphoblastic LeukemiaAntigen (CALLA) (Ritz et al, 283 *Nature* 583–585 (1980)) and can be used if the target cells express CALLA such as in the disease of acute lymphoblastic leukemia. Similarly, the monoclonal antibody anti-B4 is a murine $IgG_1$, that binds to the CD19 antigen on B cells (Nadler et al, 131 *J. Immunol.* 244–250 (1983)) and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH which binds to melanocytes can be used for the treatment of melanoma.

Cancers of the breast and testes can be successfully targeted with estrogen (or estrogen analogues) or androgen (or androgen analogues) respectively as cell binding agents.

Preparation of Cytotoxic Agents or Conjugates

Conjugates of the maytansinoid derivatives of the invention and a cell binding agent can be formed using any techniques presently known or later developed. The maytansinoid ester can be modified to yield a free amino group and then linked to an antibody or other cell binding agent via an acid-labile linker, or a photolabile linker. The maytansinoid ester can be condensed with a peptide and subsequently linked to a cell binding agent to produce a peptidase-labile linker. The maytansinoid ester can be treated to yield a primary hydroxyl group, which can be succinylated and linked to a cell binding agent to produce a conjugate that can be cleaved by intracellular esterases to liberate free drug. Most preferably, the maytansinoid esters are treated to create a free or protected thiol group, and then one or many disulfide or thiol-containing maytansinoid derivatives are covalently linked to the cell binding agent via disulfide bond(s).

Representational conjugates of the invention are antibody/maytansinoid derivatives, antibody fragment/maytansinoid derivatives, epidermal growth factor (EGF)/maytansinoid derivatives, melanocyte stimulating hormone (MSH)/maytansinoid derivatives, thyroid stimulating hormone (TSH)/maytansinoid derivatives, estrogen/maytansinoid derivatives, estrogen analogue/maytansinoid derivatives, androgen/maytansinoid derivatives, androgen analogue/maytansinoid derivatives.

Maytansinoid conjugates of antibodies, antibody fragments protein hormones, protein growth factors and other proteins are made in the same way. For example, peptides and antibodies can be modified with crosslinking reagents such as N-succinimidyl 3-(2-pyridyldithio)propionate, 4-succinimidyl-oxycarbonyl-α-methyl-α-(2-pyridyldithio)-toluene (SMPT), N-succinimidyl-3-(2-pyridyldithio)-butyrate (SDPB), 2-iminothiolane, or S-acetylsuccinic anhydride by known methods. See, Carlsson et al, 173 *Biochem. J.* 723–737 (1978); Blattler et al, 24 *Biochem.* 1517–1524 (1985); Lambert et al, 22 *Biochem.* 3913–3920 (1983); Klotz et al, 96 *Arch. Biochem. Biophys.* 605 (1962); and Liu et al, 18 Biochem. 690 (1979); Blakey and Thorpe, 1 *Antibody, Immunoconjugates & Radiopharmaceuticals*, 1–16 (1988), Worrell et al 1 *Anti-Cancer Drug Design* 179–184 (1986). The cell binding agent containing free or protected thiol groups thus derived is then reacted with a disulfide- or thiol-containing maytansinoid to produce conjugates. The conjugates can be purified by HPLC or by gel filtration.

Similarly, for example, estrogen and androgen cell binding agents such as estradiol and androstenediol can be esteriliad at the C-17 hydroxy group with an appropriate disulfide-containing carboxylic acid using e.g. dicyclohexylcarbodiimide as a condensing agent. Examples of such carboxylic acids that can be employed are 3-(2-pyridyldithio)propanoic acid, 3-methyldithiopropanoic acid, and 3-phenyldithiopropanoic acid. Esterification of the C-17 hydroxy group can also be achieved by reaction with an appropriately protected thiol group-containing carboxylic acid chloride such as 3-S-acetylpropanoyl chloride. Other methods of esterification can also be employed as described in the literature (Haslam, 36 *Tetrohedron* 2409–2433 (1980)). The protected or free thiol-containing androgen or estrogen can then be reacted with a disulfide or thiol-containing maytansinoid to produce conjugates. The conjugates can be purified by column chromatography on silica gel or by HPLC.

Preferably monoclonal antibody or cell binding agent/maytansinoid conjugates are those that are joined via a disulfide bond, as discussed above, that are capable of delivering maytansinoid molecules. Such cell binding conjugates are prepared by known methods such as modifying monoclonal antibodies with succinimidyl pyridyl-dithiopropionate (SPDP) (Carlsson et al, 173 *Biochem. J.* 723–737 (1978)). The resulting thiopyridyl group is then displaced by treatment with thiol-containing maytansinoids to produce disulfide linked conjugates. Alternatively, in the case of the aryldithiomaytansinoids, the formation of the cell binding conjugate is effected by direct displacement of the aryl-thiol of the maytansinoid by sulfhydryl groups previously introduced into antibody molecules. Conjugates containing 1 to 10 maytansinoid drugs linked via a disulfide bridge are readily prepared by either method.

More specifically, a solution of the dithiopyridyl modified antibody at a concentration of 1 mg/ml in 0.1M potassium phosphate buffer, at pH 7.0 containing 1 mM EDTA is treated with the thiol-containing maytansinoid (1.25 molar equivalent/dithiopyridyl group). The release of pyridine-2-thione from the modified antibody is monitored spectrophotometrically at 343 nm and is complete in about 30 min. The antibody-maytansinoid conjugate is purified and freed of unreacted drug and other low molecular weight material by gel filtration through a column of Sephadex G-25. The number of maytansinoids bound per antibody molecule can be determined by measuring the ratio of the absorbance at 252 nm and 280 nm. An average of 1–10 maytansinoid molecules/antibody molecule can be linked via disulfide bonds by this method.

Antibody-maytansinoid conjugates with non-cleavable links can also be prepared. The antibody can be modified with crosslinking reagents such as succinimidyl 4-(N-maleimidomethyl)-cyclohexane-1-carboxylate (SMCC), sulfo-SMCC, m-maleimidobenzoyl-N-hydroxysuccinimide ester (MBS), sulfo-MBS or succinimidyl-iodoacetate, as described in the literature, to introduce 1–10 reactive groups. See, Yoshitake et al, 101 *Eur. J. Biochem.* 395–399 (1979); Hashida et al, *J. Applied Biochem.* 56–63 (1984); and Liu et al, 18 *Biochem.* 690–697 (1979). The modified antibody is then reacted with the thiol-containing maytansinoid derivative to produce a conjugate. The conjugate can be purified by gel filtration through a Sephadex G-25 column.

The modified antibodies are treated with the thiol-containing maytansinoid (1.25 molar equivalent/maleimido group). The mixtures are incubated overnight at about 4° C. The antibody-maytansinoid conjugates are purified by gel filtration through a Sephadex G-25 column. Typically, an average of 1–10 maytansinoids/antibody are linked.

A preferred method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result.

Cytotoxicity Assays

Cytotoxicity of the maytansinoids and their antibody conjugates to non-adherent cell lines such as Namalwa and HL-60 can be measured by back-extrapolation of cell proliferation curves as described in Goldmacher et al, 135 *J. Immunol.* 3648–3651 (1985). Cytotoxicity of these compounds to adherent cell lines such as SKBR3 and KB can be determined by clonogenic assays as described in Goldmacher et al, 102 *J. Cell Biol.* 1312–1319 (1986).

Therapeutic Agent and Method for Killing Selected Cell Populations

The present invention also provides atherapeutic agent for killing selected cell populations comprising:

(a) a cytotoxic amount of one or more maytansinoids linked to a cell binding agent, and (b) a pharmaceutically acceptable carrier, diluent or excipient.

Similarly, the present invention provides a method for killing selected cell populations comprising contacting a cell population or tissue suspected of containing cells from said selected cell population with a cytotoxic amount of a cytotoxic agent comprising one or more maytansinoids linked to a cell binding agent.

The cytotoxic agent is prepared as described above.

Suitable pharmaceutically acceptable carriers, diluents, and excipients are well known and can be determined by those of skill in the art as the clinical situation warrants.

Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The method for killing selected cell populations can be practiced in vitro, in vivo, or ex vivo.

Examples of in vitro uses include treatments of autologous bone marrow prior to their transplant into the same patient in order to kill diseased or malignant cells; treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by the skilled artisan.

For clinical ex vivo use to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplantation in order to prevent GVHD, treatment can be carried out as follows. Bone marrow is harvested from the patient or other individual and then incubated in medium containing serum to which is added the cytotoxic agent of the invention, concentrations range from about 10 $\mu$M to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels. Examples of suitable protocols of conjugate administration are as follows. Conjugates are given daily for 5 days either as an i.v. bolus each day for 5 days, or as a continuous infusion for 5 days. Bolus doses are given in 50 to 100 ml of normal saline to which 5 to 10 ml of human serum albumin has been added. Continuous infusions are given in 250 to 500 ml of normal saline, to which 25 to 50 ml of human serum albumin has been added, per 24 hour period. Dosages will be 10 $\mu$g to 100 mg/kg of body weight per day, i.v. (range of 1 ng to 10 mg/kg per day). Four weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; vital infections, such as CMV infection, HIV infection, AIDS, etc,; and parasite infections, such as giardiasis, amoebiasis, schistosomiasis, and others as determined by one skilled in the art.

EXAMPLES

The invention will now be illustrated by reference to nonlimiting examples. Unless otherwise stated, all percents, ratios, parts, etc. are by weight.

Example 1

Synthesis of Maytansinoid Derivatives

Melting points were determined on a Electrothermal melting point apparatus. Proton magnetic resonance ($^1$H NMR) spectra were obtained on a Varian EM360 spectrometer at 60 MHz or on a Bruker AM300 machine at 300 MHz. Chemical shifts are reported in $\delta$ values relative to an internal tetramethylsilane (TMS) standard. UV spectra were recorded on a Perkin Elmer $\lambda$4A spectrophotometer. Optical rotations were determined using a Perkin Elmer model 241 polarimeter. A Rainin HPX instrument equipped with a Gilson variable wavelength UV detector and a Waters Radialpak C-18 column was-used for HPLC analyses. Elemental analyses were performed by Atlantic Microlabs, Atlanta, Ga.

3-Methyldithio-propanoic acid (3b). To a stirred solution of 3-mercaptopropanoic acid (2b) (5.00 g. 0.047 mol) in water (150 ml), cooled in an ice bath, was added methyl methanethiosulfonate (6.54 g. 0.052 mol) in absolute ethanol (75 ml). The reaction mixture was stirred overnight at room temperature. The mixture was then diluted with saturated, aqueous NaCl (400 ml) and extracted with ether (3×150 ml). The combined ether extracts were washed with saturated NaCl, dried over $Na_2SO_4$ and concentrated. The residue was distilled to afford a colorless liquid (6.47 g, 90%): $bp_{1.0}$105° C. $^1$H NMR($CDCl_3$) $\delta$2.3 (3H, s), 2.8 (4H, m), 11.2 (1H, s).

4-methyrdithio-butanoic acid (3c). To a stirred solution of bis-(3-carboxypropyl)-disulfide (1.00 g, 4.20 mmol) in methanol (20 ml) was added a solution of dithiothreitol (0.647 g, 4.20 mmol) in $H_2O$ (20 ml). A solution of 10M NaOH (0.842 ml, 8.42 mmol) was then added and the mixture was allowed to stir at room temperature overnight to effect complete reduction. Methyl methanethiolsulfonate (1.17 g, 9.24 mmol) was added and the reaction mixture allowed to stir for another three hours. The mixture was then diluted with saturated, aqueous NaCl (150 ml), acidified (aqueous HCl), and extracted with ethyl ether (3×100 ml). The combined organic layers were washed with saturated NaCl, dried (Na$_2$SO$_4$), concentrated and the concentrate was chromatographed on silica gel eluting with methylene chloride/ethyl acetate to give 0.867 g (56%) of a clear liquid. $^1$H NMR (CDCl$_3$) δ2.1 (2H, m), 2.4 (3H, s), 2.4 (2H, m), 2.7 (2H, m), 11.1 (1H, s).

5-Mercaptopentanoic acid (2d). Compound 2d was prepared by a modification of a literature method (Khim et al, 37 J. Org. Chem. 2714–2720 (1972)). To a stirred solution of 5-bromopentanoic acid (1.80 g, 0.01 mol) in absolute ethanol (25 ml) was added thiourea (0.761 g, 0.01 mol) and the reaction mixture was refluxed for 6 hours. A solution of 50% aqueous NaOH (20 ml) was then added and the mixture refluxed for an additional two hours. The mixture was then diluted with water (100 ml), acidified (aqueous HCl), and extracted with ethyl acetate (4×50 ml). The combined organic layers were dried over sodium sulfate and evaporated under reduced pressure. The residue was chromatographed over silica gel eluting with methylene chloride/ethyl acetate to give 0.885 g (66%) of a colorless liquid. $^1$H NMR (CDCl$_3$) δ1.3 (1H, t), 1.6 (4H, m), 2.4 (4H, m), 11.5 (1H, s).

5-Methyldithio-pentanoic acid (3d). To a stirred solution of 5-mercaptopentanoic acid (2d) (0.500 g, 3.73 mmol) in water (20 ml) was added a solution of methyl methanethiosulfonate (0.517 g, 4.10 mmol) in absolute ethanol (5 ml) and the mixture was stirred at room temperature for 3 hours. The mixture was then diluted with aqueous, saturated NaCl (100 ml) and extracted with ethyl ether (3×100 ml). The combined organic layers were washed with saturated NaCl, dried (Na$_2$SO$_4$), evaporated under reduced pressure and the concentrate was chromatographed over silica eluting with methylene chloride/ethyl acetate to yield 0.602 g (90%) white crystals: mp 42°–44° C. $^1$H NMR (CDCl$_3$) δ1.7 (4H, m), 2.4 (3H, s), 2.4 (2H, m), 2.7 (2H, m), 11.1 (1H, s).

3-Phenyldithio-propanoic acid (4a). To a stirred solution of diphenyl disulfide (3.0 g, 13.8 mmol) in a mixture of ether (10 ml) and methanol (20 ml), under a nitrogen atmosphere, at room temperature was added a solution of 3-mercaptopropanoic acid (2b) (0.49 g, 4.6 mmol) in ether (5 ml), followed by a solution of 10M NaOH (0.46 ml, 4.6 mmol). The reaction mixture was stirred at room temperature for 20 hours, then stripped of the solvents under reduced pressure. The product was purified by column chromatography on silica gel eluting with ethyl acetate/hexane. The product was obtained as a white solid (0.56 g, 56.6%), mp 57°–59° C. NMR (CDCl$_3$, TMS) δ2.6–3.0 (4H, m), 7.1–7.6 (5H, m), 10.6 (1H, s).

3-(4-Nitrophenyldithio)-propanoic acid (4b). To a stirred solution of bis-(4-nitrophenyl)-disulfide (3.00 g, 9.73 mmol) dissolved in a mixture of THF (200 ml) and methanol (50 ml) was added 3-mercaptopropanoic acid (2b) (0.688 g, 6.49 mmol). One drop of a solution of 10N NaOH was then added to the mixture and the reaction stirred for one hour. The reaction mixture was then diluted with saturated NaCl (100 ml) and extracted with ethyl acetate (3×75 ml). The combined organic layers were dried over sodium sulfate, evaporated under reduced pressure and the product was chromatographed over silica gel eluting with methylene chloride/ethyl acetate to yield 0.885 g (53%) of a light yellow solid; mp 98°–100° C. $^1$H NMR (CD$_3$COCD$_3$) δ2.8 (2H, m), 3.1 (2H, m), 7.8 (2H, d), 8.2 (2H, d).

N-methyl-N-methyldithioacetoyl-L-alanine (5a). To a stirred solution of 1-(3-dimethylaminopropyl)-3-ethylcarbodiimide hydrochloride (2.99 g, 15.6 mmol) and triethylamine (1.58 g, 15.6 mmol) in dry CH$_2$Cl$_2$ (40 ml) at 0° C. was added a solution of methyldithioacetic acid (Singh et al, 104 Anal. Biochem. 51–58 (1980) (2a) (1.66 g, 12.0 mmol) in dry CH$_2$Cl$_2$ (20 ml). A solution of 4-dimethylaminopyridine (0.073 g, 0.60 mmol) in dry CH$_2$Cl$_2$ (2 ml) was added and the mixture stirred for 45 min. at 0° C. A mixture of N-methyl-L-alanine (0.619 g, 6.00 mmol) and triethylamine (0.607 g, 6.00 mmol) in dry DMF (30 ml) was then added and the mixture stirred at 0° C. for two hours. The reaction mixture was diluted with water (100 ml), stirred for another thirty minutes, then acidified (aqueous HCl) and extracted with ethyl acetate (4×75 ml). The combined organic layers were washed several times with water, dried over Na$_2$SO$_4$, and evaporated under reduced pressure. The residue was chromatographed over silica gel eluting with methylene chloride ethyl acetate to yield 0.25 g (19%) of a pale yellow oil. $^1$H-NMR (CDCl$_3$) δ1.4 (3H, d), 2.4 (3H, s), 2.9, 3.0 (total 3H, 2s), 3.6 (2H, s), 4.7, 5.2 (total 1H, 2q), 9.8 (1H, s).

N-methyl-N-(3-methyldithio-propanoyl)-L-alanine (5b). To a stirred solution of 3-methyldithiopropanoic acid (3b) (1.00 g, 6.57 mmol) in dry THF (20 ml) at −10° C. under argon was added isobutylchloroformate (0.897 g, 6.57 mmol) and triethylamine (0.665 g, 6.57 mmol) and the reaction mixture was stirred for 15 minutes. A mixture of N-methyl-L-alanine (0.677 g, 6.57 mmol) and triethylamine (1.33 g, 13.14 mmol) in water (10 ml) was added and the reaction mixture was stirred at room temperature overnight. The mixture was then diluted with water (50 ml), acidified (aqueous HCl), and extracted with ethyl acetate (4×50 ml). The combined organic layers were dried over sodium sulfate, the solvent evaporated under reduced pressure and the residue chromatographed over silica gel eluting with methylene chloride/ethyl acetate to yield 0.556 g (34%) white crystals: mp 98°–100° C. $^1$H NMR (CDCl$_3$) δ1.3 (3H, d), 2.2 (3H, s), 2.7 (4H, m), 4.5 (1H, q), 10.7 (1H, s). Anal. Calculated for C$_8$H$_{15}$NO$_3$S$_2$: C, 40.49; H, 6.37; N, 5.90; mol wt. 237.33. Found: C, 40.42; H, 6.41; N, 5.93.

N-methyl-N-(4-methyldithio-butanoul)-L-alanine (5c). To a stirred solution of 4-methyldithiobutanoic acid (3c) (0.200 g, 1.20 mmol) in dry THF (10 ml) at −20° C. under Argon was added isobutyl chloroformeta (0.164 g, 1.20 mmol) and triethylamine (0.121 g, 1.20 mmol) and the mixture was stirred for twenty minutes. A mixture of N-methyl-L-alanine (0.124 g, 1.20 mmol) and triethylamine (0.243 g, 2.40 mmol) in water (5 ml) was then added and the reaction mixture was stirred at room temperature for five hours. The reaction mixture was then treated as described above for 5b giving the title compound as white crystals (0.135 g, 44%): mp 92°–93° C. $^1$H NMR (CDCl$_3$) δ1.4 (3H, d), 2.0 (2H, m), 2.3 (3H, s), 2.7 (4H, m), 2.9 (3H, s), 5.1 (1H, q), 10.5 (1H, s).

N-methyl-N-(5-methyldithio-pentanoyl)-L-alanine (5d). To a stirred solution of 5-methyldithio-pentanoic acid (3d) (0.202 g, 1.12 mmol) in dry THF (15 ml) at −40° C. under Argon was added isobutyl chloroformate (0.153 g, 1.12 mmol) and triethylamine (0.113 g, 1.12 mmol) and the reaction mixture was stirred for 20 minutes at −10° C. A solution of N-methyl-L-alanine (0.116 g, 1.12 mmol) and triethylamine (0.227 g, 2.24 mmol) in water (5 ml) was then added and the mixture was stirred at 0° C. for five hours. The reaction mixture was treated as described above for 5b affording the title compound as white crystals (0.196 g, 66%): mp 84° C. $^1$H NMR (CDCl$_3$) δ1.4 (3H, d), 1.8 (4H, m), 2.4 (3H, s), 2.7 (4H, m), 3.0 (3H, s), 5.2 (1H, q), 10.7 (1H, s).

N-Methyl-N-(3-phenyldithio-propanoyl)-L-alanine (5e). A solution of 3-phenyldithio-propanoic acid (4a) (1.8 g, 8.4 mmol) in dry THF was stirred vigorously under a nitrogen atmosphere and cooled to −15° C. Isobutyl chloroformate (1.2 ml, 9.25 mmol) and triethylamine (1.29 ml, 9.25 mmol) were added and the reaction mixture was stirred at this temperature for ten minutes. A solution of N-methyl-L-alanine (0.87 g, 8.4 mmol) and triethylamine (1.29 ml, 9.25 mmol) in water (10 ml) was then added and the reaction mixture was stirred for fifteen minutes at −15° C. and then warmed to room temperature and stirred for an additional period of 2.5 hours. $^1$M HCl (10 ml) was added and the reaction mixture was extracted with ethyl acetate (4×50 ml). The combined organic layers were dried with $Na_2SO_4$, filtered, and evaporated under reduced pressure. The crude mixture was purified by column chromatography on silica gel eluting with ethyl acetate/hexane-containing 2% acetic acid to give a white solid (1.5 g, 60%): mp 96°–97° C. NMR ($CDCl_3$/TMS) δ1.4 (2H, d), 2.7–3.0 (7H, m), 5.2 (1H, q), 7.2–7.6 (5H, m).

N-Methyl-N-[3-(4-Nitrophenyldithio)-propanoyl]L-alanine (5f). To a stirred solution of 3-(4-nitrophenyldithio)-propanoic acid (4b) (0.100 g, 0.386 mmol) in dry THF (10 ml) at −40° C. under argon was added isobutyl chloroformate (0.053 g, 0.386 mmol) and triethylamine (0.039 g, 0.38 mmol) and the reaction stirred at 0° C. for sixty minutes. An aqueous solution (5 ml) of N-methyl-L-alanine (0.040 g, 0.386 mmol) and triethylamine (0.039 g, 0.386 mmol) was then added and the mixture stirred at 0° C. for five hours. The mixture was diluted with water (50 ml), acidified (aqueous HCl), and extracted with ethyl ether (3×25 ml). The combined organic layers were dried ($Na_2SO_4$), and the solvent evaporated under reduced pressure. The residue was chromatographed over silica gel eluting with methylene chloride/ethyl acetate to yield 0.048 g (36%) yellow crystals: mp 74°–77° C. NMR ($CDCl_3$) δ1.4 (3H, d), 2.6–3.4 (4H, m), 2.9 (3H, s), 5.1 (1H, q), 7.6–8.3 (4H, 2d).

Esterification of Maytansinol. In a typical experiment, a solution of the carboxylic acid 5 (133 μmols) in dry methylene chloride (0.3 ml), was stirred under an argon atmosphere, and treated sequentially with solutions of dicyclohexylcarbodiimide (160 μmol) in methylene chloride (0.2 ml), 1M $ZnCl_2$ in ether (26.2 μmol) and maytansinol (15 mg, 26.6 μmol) in methylene chloride (0.3 ml). The reaction mixture was stirred at room temperature for three hours, and then filtered and the filtrate evaporated under reduced pressure. Preparative TLC of the crude mixture on silica gel, eluting twice with 6% methanol in $CHCl_3$ gave two major UV absorbing bands. Both bands were isolated by extraction with ethyl acetate and characterized by NMR spectroscopy.

Esterification of Maytansinol with N-methyl-N-(methyldithio-propanoyl)-L-alanine. A solution of the carboxylic acid 5b (31.5 mg., 133 μmol) in dry $CH_2Cl_2$ (0.3 ml) was stirred under an argon atmosphere and treated sequentially with solutions of dicyclohexyl-carbodiimide (33 mg, 160 μmol) in $CH_2Cl_2$, 1M $ZnCl_2$ in ether (26.6 μmol), and maytansinol (15 mg, 26.6 μmol) in $CH_2Cl_2$ (0.3 ml). The reaction mixture was stirred at room temperature for three hours and then filtered and the solvent evaporated under reduced pressure. Preparative TLC on silica gel, eluting twice with 6% methanol in $CHCl_3$ gave two strong UV absorbing bands with Rf values of 0.6 and 0.7 respectively. Both bands were isolated by extraction with ethyl acetate. NMR spectra and cytotoxicity analyses confirmed that the higher Rf band was the D-aminoacyl ester (45%) while the lower band was the desired L-aminoacyl ester 6b (55%). Both bands were further purified by HPLC on a Waters Radialpak C-18 column, eluting at a flow rate of 1.5 ml/min with a linear gradient of acetonitrile in $H_2O$ (55% $CH_3CN$ to 80% $CH_3CN$, over 10 min). Under these conditions both isomers had an identical retention time of 7.3 min. NMR ($CDCl_3$) L-aminoacyl isomer: δ0.84(3H, s), 1.11–1.23 (1H, m), 1.31 (3H, d, J=6 Hz), 1.35 (3H, d, J=7 Hz), 1.46–1.52 (1H, m), 1.68 (3H, s), 1.97 (1H, d, J=9 Hz), 2.24 (1H, dd, J=12 Hz and 15 Hz), 2.30 (3H, s), 2.65 (1H, dd, J=12 Hz and 15 Hz), 2.73–2.86 (2H, m), 2.90 (3H, s), 2.92–3.03 (2H, m), 3.08 (1H, d, J=9 Hz), 3.14 (1H, d, J=12 Hz), 3.28 (3H, s), 3.39 (3H, s), 3.54 (1H, d, J=9 Hz), 3.72 (1H, d, J=13 Hz), 4.02 (3H, s), 4.31 (1H, t, J=11 Hz), 4.82 (1H, dd, J=3 Hz and 12 Hz), 5.45 (1H, q, J=7 Hz), 5.69 (1H, dd, J=9 Hz and 15 Hz), 6.25 (1H, s), 6.47 (1H, dd, J=11 Hz and 15 Hz), 6.67 (1H, d, J=1.5 Hz), 6.77 (1H, d, J=11 Hz), 6.85 (1H, d, J=1.5 Hz).

Esterification of Maytansinol with N-methyl-N-(methyldithiobutanoyl)-L-alanine. A solution of the carboxylic acid 5c (8.9 mg, 35.5 μmol) in $CH_2Cl_2$ (0.15 ml) was stirred under an atmosphere of argon, and treated sequentially with solutions of DCC (8.8 mg, 42.6 μmol) in $CH_2Cl_2$, 1M $ZnCl_2$ (7.1 μmol) in ether and maytansinol (4.0 mg, 7.1 μmol) in $CH_2Cl_2$. The reaction mixture was stirred at room temperature for 3 hours, and then filtered and the filtrate was evaporated under reduced pressure. The residue was purified by preparative TLC on silica gel, eluting twice with 7% methanol in $CHCl_3$. Two new UV absorbing bands (Rf=0.65 and 0.75) were obtained. The products were isolated by extraction with ethyl acetate. The higher Rf band was determined to be the D-aminoacyl ester 6d (41%), while the lower Rf band was the desired L-aminoacyl ester 6c (59%). Both isomers were further purified by HPLC using a Waters Radialpak C-18 column, eluting at a flow rate of 2 ml/min, with a linear gradient of acetonitrile in water (50% to 80% acetonitrile, over 10 minutes). Under these conditions the D-aminoacyl ester had a retention time of 7.4 minutes, while the L-aminoacyl isomer had a retention time of 7.6 min.

Esterification of Maytaneinol with N-methyl-N-(phenyldithio-propanoyl)-L-alanine. A solution of the carboxylic acid 5e (31.5 mg, 105 μmol) in $CH_2Cl_2$ (0.4 ml) was stirred under argon and treated sequentially with solutions of DCC (26 mg, 126 μmol) in $CH_2Cl_2$, 1M $ZnCl_2$ (17.7 μmol) in ether and maytansinol (10 mg, 17.7 μmol) in $CH_2Cl_2$ (0.2 ml). The reaction mixture was stirred at room temperature for three hours. The precipitate was removed by filtration and the filtrate concentrated under reduced pressure. Preparative TLC of the residue on silica gel, eluting twice with 5% methanol in $CHCl_3$ gave two strongly UV absorbing bands with Rf values of 0.5 and 0.6. The two products were isolated by extraction with ethyl acetate and characterized by NMR spectroscopy. The higher Rf band was found to be the D-aminoacyl ester 6f (45%) of maytansinol and the lower band was the L-aminoacyl ester 6e (55%). The overall yield of ester from maytansinol was 44%. The products were further purified by HPLC on a Waters Radialpak C-18 column, eluting at a flow rate of 1.5 ml/min. with a linear gradient of acetonitrile in water (70% to 90% acetonitrile, over 10 min). Under these conditions both isomers had an identical retention time of 6.0 min. NMR ($CDCl_3$) L-aminoacyl isomer 6e:

δ0.82 (3H, s), 1.11-1.25 (1H, m), 1.33 (3H, d, J=3 Hz), 1.61 (3H, s), 1.63 (3H, d, J=14 Hz), 2.19 (1H, dd, J=13 Hz and 15 Hz), 2.61 (1H, dd, J=12 Hz and 15 Hz), 2.78 (3H, s), 2.68-3.03 (2H, m), 3.07 (1H, d, J=9 Hz), 3.20 (3H, s), 3.38 (3H, s), 3.53 (1H, d, J=9 Hz), 3.63 (1H, d, J=13 Hz), 3.68 (3H, s), 4.01 (3H, s), 4.30 (1H, t, J=11 Hz), 4.79 (1H, dd, J=3 Hz and 8 Hz), 5.43 (1H, q, J=7 Hz), 5.68 (1H, dd, J=9 Hz and 15 Hz), 6.23 (1H, s), 6.45 (1H, dd, J=12 Hz and 15 Hz), 6.60 (1H, d, J=1.5 Hz), 6.75 (1H, d, J=12 Hz), 6.77 (1H, d, J=1.5 Hz), 7.22-7.40 (5H, m).

Reduction of Maytansinoids. The disulfide-containing esters 6 of maytansinol were reduced to the thiol-containing maytansinoids 7 with dithiothreitol by the methods outlined below. In all cases the reactions were performed at 4° C. and the products were purified by HPLC.

Reduction of Maytansinoid (6b). A solution of the methyl disulfide ester 6b (0.89 μmol) in ethanol (0.23 ml) and 0.1M potassium phosphate buffer pH 7.5 (0.16 ml) containing 1 mM EDTA was cooled in ice, under an argon atmosphere and treated with a solution of 100 mM dithiothreitol (1.33 μmol). The progress of reduction was followed by HPLC and judged to be complete after ten hours. The thiol-containing maytansinoid 7b was purified by HPLC using a Waters Radialpak C-18 column at a flow rate of 1.5 ml/min. eluting with a linear gradient of acetonitrile in water (55%-80% acetonitrile, over 10 min). Under these conditions the product eluted as a single peak with a retention time of 5.4 minutes. The presence of one mole of sulfhydryl group/mol product was confirmed using Ellman's assay. The product was further characterized by NMR spectroscopy. NMR (CDCl$_3$): δ0.84 (3H, s), 1.33 (3H, d, J=5 Hz), 1.35 (3H, d, J=5 Hz), 1.60 (3H, s), 1.68 (3H, s), 2.22 (1H, dd, J=3 Hz and 14 Hz, 2.60-2.82 (2H, m), 2.88 (3H, s), 3.08-3.20 (2H, m), 3.25 (3H, s), 3.39 (3H, s), 3.55 (1H, d, J=9 Hz), 3.71 (1H, d, J=12 Hz), 4.02 (3H, s), 4.32 (1H, t, J=10 Hz), 4.81 (1H, dd, J=3 Hz and 12 Hz), 5.45 (1H, q, J=7 Hz), 5.67 (1H, dd J=9 Hz and 15 Hz), 6.25 (1H, s), 6.47 (1H, dd, J=11 Hz and 15 Hz), 6.70 (1H, d, J=1.5 Hz), 6.75 (1H, d, J=11 Hz), 6.86 (1H, d, J=1.5 Hz).

Reduction of Maytansinoid (6e). A solution of the phenyldisulfide ester 6e (0.463 μmol) in ethanol (0.22 ml) and 0.1M potassium phosphate buffer. pH 7.5 (0.18 ml) containing 2 mM EDTA was cooled in ice and treated with a solution of 20 mM dithiothreitol (0.69 μmol, 0.035 ml). The progress of the reaction was monitored by HPLC and judged to be complete in 40 minutes. The thiol-containing maytansinoid generated in this manner was purified as described above and found to be identical to 7b.

Example 2

In Vitro Cytotoxicity Assays

The disulfide-containing maytansinoid drugs of the invention were evaluated for their ability to suppress proliferation of various human tumor cell lines in vitro. Two adherent cell lines KB (human epidermoid carcinoma) and SKBR3 (human breast tumor) and the non-adherent cell line, Namalwa (Burkitt's lymphoma) were used for the assessment of cytotoxicity of these compounds. Cells were exposed to the compounds for 24 hours and the surviving fractions of cells were measured in direct assays. (KB and SKBR3 were assayed for plating efficiency (Goldmacher et al, 102 *J. Cell. Biol.* 1312-1319 (1986) and Namalwa was assayed by growth back-extrapolation (Goldmacher et al, 135 *J. Immunol.* 3648-3651 (1985)). IC$_{50}$ values were then calculated from these data. The results of these tests are presented in Table 1.

TABLE 1

Cytotoxicity of New Maytansinoid Derivatives
IC$_{50}$ (M) values for 24 hour exposure

| | Cell Line | | |
|---|---|---|---|
| Compound | KB | SKBR3 | NAMALWA |
| 1a | $3.4 \times 10^{-11}$ | $1.1 \times 10^{-10}$ | $4 \times 10^{-10}$ |
| 6b | $1.1 \times 10^{-11}$ | $1.1 \times 10^{-11}$ | $6.4 \times 10^{-9}$ |
| 6c | $8.5 \times 10^{-12}$ | $3.8 \times 10^{-11}$ | $3.2 \times 10^{-9}$ |
| 6d | $1.9 \times 10^{-10}$ | nd | $1.3 \times 10^{-8}$ |
| 6e | $1.0 \times 10^{-10}$ | nd | $6 \times 10^{-10}$ |
| 6f | $2.0 \times 10^{-9}$ | nd | $8 \times 10^{-9}$ |
| 7b | $6 \times 10^{-10}$ | $<10^{-11}$ | $1 \times 10^{-8}$ |
| 7c | $4 \times 10^{-10}$ | nd | nd |

The L-aminoacyl isomers 6b and 6c are highly toxic towards KB and SKBR3 cells with IC$_{50}$ values of $\leq 1 \times 10^{-11}$M while the corresponding phenyl-dithio analog 6e has an IC$_{50}$ value of $1 \times 10^{-10}$M on KB cells. The methyl-dithio analogs 6b and 6c are 3-10 fold more toxic than maytansine which has an IC$_{50}$ of $3 \times 10^{-11}$M and $1 \times 10^{-10}$M to KB and SKBR3 cells respectively. These two compounds, however, are somewhat less toxic, IC$_{50} \geq 3 \times 10^{-9}$M, than maytansine, IC$_{50} = 4 \times 10^{-10}$M, to Namalwa cells while the phenyl-dithio compound 6e is almost as toxic, IC$_{50} = 6 \times 10^{-10}$M, as maytansine. The D-aminoacyl isomers 6d and 6f were at least 20 times less toxic than their L counterparts, 6c and 6e, to all three cell lines. The free thiol-containing maytansinoids are also very toxic to KB and SKBR3 cells with IC$_{50}$ values for 7b of $6 \times 10^{-10}$M and $<10^{-11}$M respectively.

Since the methyldithio-maytansinoids are even more toxic than maytansine to solid tumor cell lines like KB and SKBR3, a wider panel of solid tumor cell lines was tested in a manner analogous to that described above to see whether this was a general phenomenon. The results are summarized in Table 2.

TABLE 2

IN VITRO CYTOTOXICITY OF MAYTANSINE (1a) AND
MAYTANSINOID DERIVATIVE (6b)
TOWARDS DIFFERENT CELL LINES

| | IC$_{50}$ (24 hr. exposure) Molar | |
|---|---|---|
| CELL LINE | Maytansine | May-CH$_2$CH$_2$SSMe (6b) |
| KB (Epidermoid Carcinoma) | $3.4 \times 10^{-11}$ | $1.1 \times 10^{-11}$ |
| SKBR3 (Breast adenocarcinoma) | $1.1 \times 10^{-10}$ | $1.2 \times 10^{-11}$ ($1 \times 10^{-13}$, 72 hr exposure) |
| SW620 (Colon adenocarcinoma) | $>10^{-10}$ | $4 \times 10^{-11}$ |
| A498 (Renal carcinoma) | $>10^{-10}$ | $1 \times 10^{-10}$ |
| Ovcar3 (Ovarian carcinoma) | $1.0 \times 10^{-10}$ | $5 \times 10^{-11}$ |
| Namalwa (Burkitt's lymphoma) | $4 \times 10^{-10}$ | $6 \times 10^{-9}$ |
| HL60 (Promyelocytic leukemia) | $5 \times 10^{-10}$ | $8 \times 10^{-10}$ |

The methyldithio compound 6b was very toxic to SW620 (colon adenocarcinoma) and A498 cells (renal carcinoma) with IC$_{50}$ values of $4 \times 10^{-11}$M and $1 \times 10^{-10}$M respectively, while maytansine was non-toxic (surviving fraction=100%) even at $1 \times 10^{-10}$M to these cell lines. Compound 6b was twice as cytotoxic, IC$_{50} = 5 \times 10^{-11}$M, as maytansine to the ovarian cancer cell line OVCAR3. The high cytotoxicity of the methyl-dithio maytansinoids to adherent cell lines is an unexpectedly superior property of these compounds and indicates that cancers caused by solid tumors are good targets for treatment with conjugates of these compounds with appropriate cell targeting agents.

Example 3

Conjugation of Antibodies

Conjugation of Maytansinoid 7b to Antibodies via Disulfide links: The conjugation of the thiol-containing maytansinoid 7b to antibodies via disulfide links was performed in two steps. In the first step dithiopyridyl groups were introduced into antibodies using succinimidyl pyridyldithiopropionate (SPDP) as described by Carlsson et al. The thiopyridyl groups were then displaced by reaction with the maytansinoid 7b to produce a conjugate.

Preparation of Antibody-SS-Maytansinoid Conjugates. Antibodies anti-B4, anti-T9 and A7 were modified with SPDP as described in the literature. Between 1 to 10 dithiopyridyl groups were introduced on the average per antibody molecule.

A solution of the dithiopyridyl modified antibody at a concentration of 1 mg/ml in 0.1M potassium phosphate buffer pH 7.0 containing 1 mM EDTA at 25° C. was treated with the thiol-containing maytansinoid 7b (1.25 molar equivalent/dithiopyridyl group). The release of pyridine-2-thione from the modified antibody was monitored spectrophotometrically at 343 nm and was found to be complete in 30 minutes. The antibody-maytansinoid conjugate was purified and freed of unreacted drug and other low molecular weight material by gel filtration through a column of Sephadex G-25. The number of maytansinoid molecules bound per antibody molecule was determined by measuring the ratio between the absorbances at 252 nm and 280 nm. An average of 1-10 maytansinoid molecules/antibody molecule can be linked via disulfide bonds by this method.

Conjugation of Maytansinoid 7b to Antibodies via a Noncleavable Thioether Link: The conjugation of the thiol-containing maytansinoid 7b was performed in two steps. The antibody was first reacted with succinimidyl maleimidomethylcyclohexane carboxylate (SMCC) to introduce maleimido groups. The modified antibody was then reacted with maytansinoid 7b forming thioether links.

Preparation of Antibody-Maytansinoid Conjugates (non-cleavable). Antibodies, anti-B4, anti-T9 and A7 were modified with SMCC as described in the literature.

The modified antibodies were treated with maytansinoid (7b) (1.25 molar equivalent/maleimido group). The mixtures were incubated overnight at 4° C. The antibody-maytansinoid conjugates were purified as described above. Typically, an average of 1-10 maytansinoid molecules/antibody molecule were linked.

Example 4

Other Methods of Linking Maytansinoids

Acid Labile Linker

Maytansinol can be esterified with N-methyl-N-(3-t-boc-aminopropanoyl)-L-alanine in the presence of dicyclohexylcarbodiimide and zinc chloride as described for 6b. Cleavage of the t-boc protecting group with trifluoroacetic acid will give a C-3 ester of maytansinol containing a terminal amino group. This amino group containing maytansinoid derivative can be linked to antibodies and other cell binding agents via an acid labile linker as previously described (Blattler et al, 24 *Biochemistry*, 1517–1524 (1985), U.S. Pat. Nos. 4,542,225, 4,569,789 and 4,764,368).

Photolabile Linker

The amino group-containing maytansinoid derivative described above can be linked to cell binding agents via a photolabile linker as previously described (Senter et al, 42 *Photochemistry and Photobiology*, 231–237 (1985), U.S. Pat. No. 4,625,014).

Peptidase Labile Linker

The amino group-containing maytansinoid described above can also be linked to cell binding agents via peptide spacer linkers. It has been previously shown that short peptide spacers between drugs and macromolecular protein carriers are stable in serum but are readily hydrolyzed by intracellular lysosomal peptidases (Trouet et al, 79 *Proc. Nat'l. Acad. Sci.*, 626–629 (1982)). The amino group-containing maytansinoid can be condensed with peptides such as Ala-Leu, Leu-Ala-Leu and Ala-Leu-Ala-Leu using condensing agents such as 1-ethyl-3-(3-dimethylaminopropyl) carbodiimide-HCl to give a peptide derivative of the maytansinoid which can then be linked to cell binding agents.

Esterase Labile Linker

Maytansinol can be esteriliad with N-methyl-N-(3-tert-butoxy-propanoyl)-L-alanine in the presence of dicyclohexylcarbodiimide and zinc chloride as previously described for 6b. Cleavage of the tert-butyl protecting group with trifluoroacetic acid gives a C-3 ester of maytansinol containing a terminal primary hydroxyl group. This maytansinoid derivative can be succinylated with succinic anhydride and then linked to a cell binding agent to produce a conjugate that can be cleaved by intracellular esterases to liberate free drug. (For examples see: Aboud-Pirak et al, 38 *Biochem. Pharmacol.*, 641–648 (1989), Laguzza et al, 32 *J. Med. Chem.*, 549–555 (1989)).

Disulfide Link Through Thiol Of N-Methyl Cysteine Or N-Methyl-Homocysteine The disulfide-containing esters 10 of maytansinol can be reduced with dithiothreitol as described for 7b to produce the thiol-containing maytansinoids 11 which can be conjugated to cell binding agents via disulfide or thioether links as previously described. (See Example 3).

Methyldithio-N-Methylcysteine (8): A solution of N-methylcysteine (Undhein, K., & Eidem, A., 23 *Acta Chem. Scandinavica* 3129–3133 (1970) (1.5 g, 11.1 mmol) in $H_2O$ (20 ml) was stirred at room temperature, under an atmosphere of argon, and treated with a solution of methyl methanethiol sulfonate (3.0 ml, 29.2 mmol) in ethanol (10 ml). The reaction mixture was stirred at this temperature for two hours and then diluted with $H_2O$ (100 ml) and washed with ether (4×40 ml). The aqueous layer was acidified to pH 2 and passed through an Amberlite IRA 93 (—OH form) column. The column was washed with water and the effluent was collected and evaporated to dryness under reduced pressure to give a white solid (1.2 g, 60%), mp 194°–5° C. NMR ($D_2O$, TMS ext. standard): $\delta 2.2(3H,s)$, $2.5(3H,s)$, $3.2(2H,d)$, $3.7(1H,q)$.

N-Acetyl-N-Methyl-Methyldithiocysteine (9): To a solution of glacial acetic acid (0.25 ml, 4.4 mmol) in dry THF (4 ml), at −20° C. under an atmosphere of $N_2$ were added, with stirring, isobutylchloroformate (0.57 ml, 4.4 mmol) and triethylamine (0.61 ml, 4.4 mmol). The reaction mixture was stirred at this temperature for 20 minutes and then treated with a solution of methyldithio-N-methylcysteine (0.4 g, 2.2 mmol) and triethylamine (0.45 ml, 3.3 mmol) in $H_2O$ and then allowed to stir overnight. The mixture was then diluted with water (25 ml) and acidified to pH 2 with HCl and extracted with ethyl acetate (4×50 ml). The combined organic layer was dried with sodium sulfate and the solvent evaporated under reduced pressure to give the product as a pale yellow solid (0.2 g, 55%) mp 137°–8° C. NMR ($CDCl_3$): 2.1(3H,s), 2.3(3H,s), 3.0(3H,s), 3.2(2H,d) and 4.8(1H,q).

Esterification Of Maytansinol With N-Acetyl-N-Methyl Methyldithiocysteine: A solution of compound 9 (15.6 mg, 0.07 mmol) in dry methylene chloride (0.45 ml) was stirred at room temperature under an argon atmosphere and treated sequentially with solutions of 1M $ZnCl_2$ in ethyl ether (0.028 mmol), DCC (17.3 mg, 0.084 mmol) in methylene chloride (0.2 ml), and maytansinol (4.0 mg, 0.007 mmol) in $CH_2Cl_2$ (0.1 ml). The reaction mixture was stirred for 3 hours and then filtered and the filtrate evaporated under reduced pressure. The residue was purified by preparative TLC on silica gel eluting with 6% methanol in $CHCl_3$. The product was isolated by extraction with ethyl acetate and further purified by HPLC on a Waters Radialpak C-18 column eluting with a linear gradient of acetonitrile in water (55–80% acetonitrile/10 min) at a flow rate of 1.5 ml/min. The L-aminoacyl ester/10a and the D-aminoacyl ester 10b of maytansinol that were obtained by this method were readily separable with retention times of 5.0 and 5.8 minutes respectively.

Example 5

Cell Cultures and In Vitro Cytotoxicity Assays

Cells of the human promyelocytic leukemia cell line, HL-60 (ATCC CCL 240) and the Burkitt's lymphoma cell line Namalwa (ATCC CRL 1432) were grown as suspension cultures in RPMI-1640 medium supplemented with 10% fetal calf serum and 2 mM L-glutamine. All other cell lines described below were grown as adherent cultures. Human spidermold carcinoma cell line, KB (ATCC CCL 17), human renal carcinoma cell line A498 (ATCC HTB 44), human colon adenocarcinoma cell lines SW620 (ATCC CCL 227) and HT-29 (ATCC HTB 38) were grown in RPMI-1640 medium supplemented with 10% fetal calf serum and 2 mM L-glutamine. Human breast carcinoma SKBR3 cells (ATCC HTB 30) were grown in DMEM supplemented with 15% fetal calf serum containing 2 mM glutamine and the human ovarian adenocarcinoma cell line OVCAR3 (ATCC HTB 161) was grown in RPMI-1640 medium supplemented with 10% fetal calf serum containing 10 μg/ml insulin and 2 mM L-glutamine.

Three different antibodies were used for conjugation via disulfide links to thiol-containing maytansinoids. In all these experiments the maytansinoid derivative 7b was used for conjugation. Conjugates were prepared with the antibodies anti-B4, which is against the B cell antigen CD19; anti-T9 (5E9) which is an anti-human transfertin receptor antibody, and A7, which is an anti-human colon cancer antibody.

Cytotoxicity assays were performed in the respective media described above. The cytotoxicity of the maytansinoids and their antibody conjugates to HL-60 and Namalwa cells was measured by back-extrapolation of cell proliferation curves. Cytotoxicity of these compounds to the rest of the cell lines was determined using a clonogenic assay as previously described.

The conjugates were assessed for in vitro cytotoxicity and the $IC_{50}$ values for cell lines Namalwa, KB, HT-29 and SW620 are summarized in Table 3.

TABLE 3

| IN VITRO CYTOTOXICITY AND SPECIFICITY OF ANTIBODY-MAYTANSINOID CONJUGATES | | |
|---|---|---|
| CELL LINE | CONJUGATE | $IC_{50}$ (Molar) (24 h exposure) |
| Namalwa | anti-B4-SS-May | $7 \times 10^{-9}$ |
|  | anti-T9-SS-May | $2 \times 10^{-9}$ |
| KB | anti-T9-SS-May | $2 \times 10^{-10}$ |
|  | anti-T9-May (non cleavable) | $4 \times 10^{-9}$ |
|  | A7-SS-May | $8 \times 10^{-9}$ (Non-Binding Antibody, 72 hr Exp.) |
| HT-29 | A7-SS-May | $1.5 \times 10^{-10}$ |
|  |  | $4 \times 10^{-11}$ (72 hr. Exp.) |
| SW620 | A7-SS-May | $1.6 \times 10^{-10}$ |

The disulfide-linked anti-B4-maytansinoid conjugate (anti-B4-SS-May) and the anti-T9-drug conjugate (anti-T9-SS-May) were both cytotoxic to Namalwa cells ($IC_{50}=7\times 10^{-9}$M and $2\times 10^{-9}$M, respectively). The disulfide-linked anti-T9 conjugate is even more toxic to KB cells with an $IC_{50}$ value of $2\times 10^{-10}$M. In order to prove the importance of an intracellularly cleavable disulfide link between antibody and drug, a conjugate in which the maytansinoid was linked to the antibody via a non-cleavable thioether bond was prepared. Thus an anti-T9-drug conjugate linked in such a non cleavable fashion was at least 20 times less toxic, ($IC_{50}=4\times 10^{-9}$M) than the corresponding disulfide linked conjugate.

Figure 5:
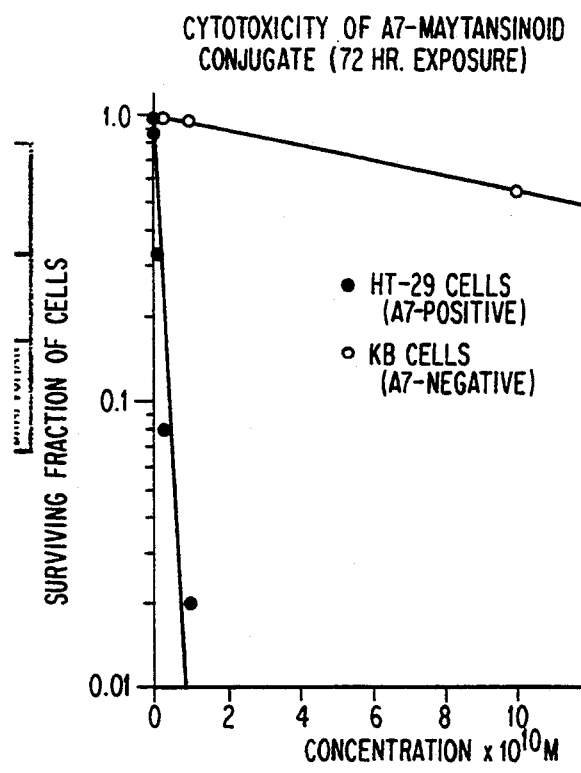
FIG. 5 shows graphically the cytotoxicity of antibody-maytansinoid conjugates.

The A7-maytansinoid conjugate is highly toxic to the colon adenocarcinoma cell lines HT-29 and SW620. The $IC_{50}$ for these cell lines after a 24 hour exposure to the conjugate were $1.5\times 10^{-10}$M and $1.6\times 10^{-10}$M, respectively. The cytotoxicity after a 72 hour exposure was even more dramatic ($IC_{50}=4\times 10^{-11}$M on HT-29 cells). Several experiments were designed to demonstrate in vitro specificity of these immunoconjugates. (Some of the data is shown graphically in FIG. 5). First, addition of an excess of unconjugated A7 antibody completely abolishes cytotoxicity of the A7-maytansinoid conjugate to HT-29 and SW620 cells at both 24 and 72 hour exposures. This observation also indicates the absence of free drug in the conjugate. Second, the conjugate prepared above with the antibody anti-B4, which does not bind to HT-29 and SW620 cells, is much less cytotoxic to these cells than the A7 conjugate. Another independent experiment that establishes specificity is the 100 fold lower cytotoxicity of the A7-maytansinoid conjugate to antigen-negative KB cells, ($IC_{50}{}^{KB}=8\times 10^{-9}$M vs $IC_{50}{}^{HT-29}=4\times 10^{-11}$M, 72 hr Exp.).

Example 6

Determination of Specific Affinity of A7-Maytansinoid Conjugates

The specific affinities of disulfide-linked A7-maytansinoid conjugates were analyzed by competition binding assays. The competition of binding of FITC-labeled A7 antibody to HT-29 and SW620 cells by unlabeled A7 and its maytansinoid conjugates were determined by direct immunofluorescence on a Becton-Dickinson FACS. The two cell lines were grown as adherent cells in tissue culture grade flasks containing Dulbecco's modified minimum essential medium with 15% fetal bovine calf serum. The cells were then trypsinized and incubated in suspension, at 37° C., for 30 minutes in the same medium in non-tissue culture grade flasks to prevent adherence of cells to the plastic. The cells were then transferred to wells of 96 well plates and resuspended in minimum essential medium containing 25% pooled human serum. Cell suspensions (0.2 ml suspension containing 100,000 cells/well) were incubated with 6 nM FITC-labeled A7. at the indicated concentrations of unlabeled antibody or maytansinoid conjugates for 1 hour at 0° C. The cells were then washed once with buffer and fixed with 1% formaldehyde in phosphate buffered saline. Mean cell fluorescence was measured on a FACS.

Figure 6A:
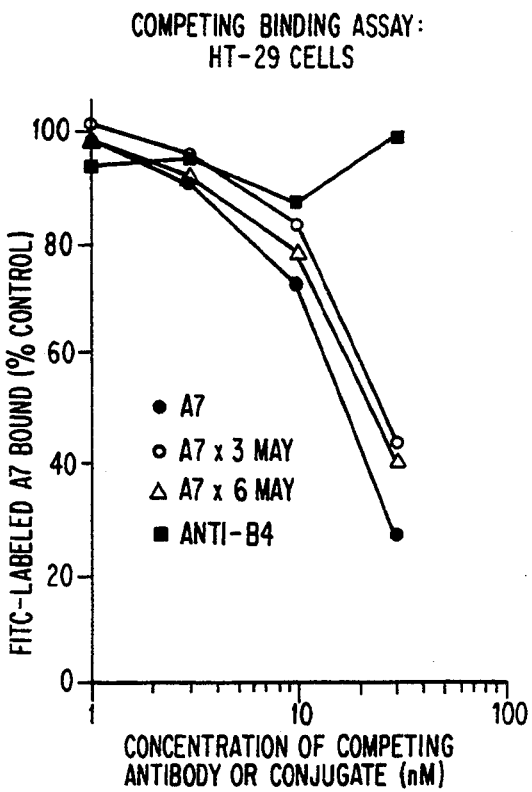
FIGS. 6(A) and 6(B) show graphically results of competitive binding assays of antibody-maytansinoid conjugates.
Figure 6B:
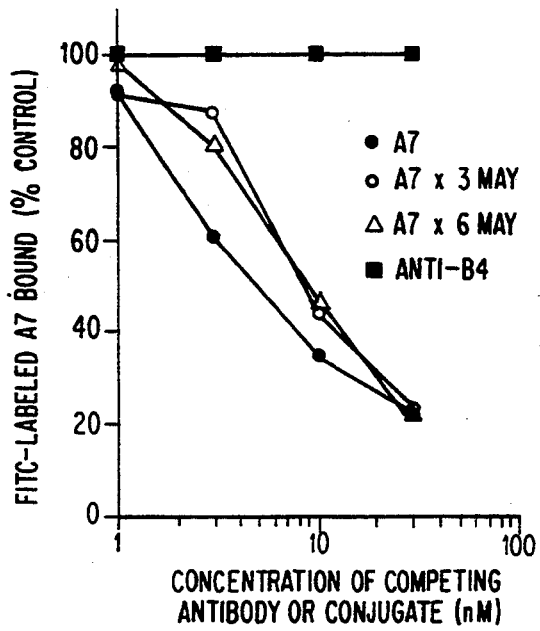

The results are shown in FIGS. 6(A) and 6(B). FIGS. 6(A) and 6(B) show that A7-maytansinoid conjugates containing between 3 to 6 drug molecules/antibody molecule bind as well as unconjugated antibody to HT-29 or SW620 cells. This indicates that the present method of conjugation of the maytansinoids to antibodies does not cause any impairment of binding to target cells.

Example 7

In Vivo Clearance Studies and Pharmacokinetics

Figure 7:
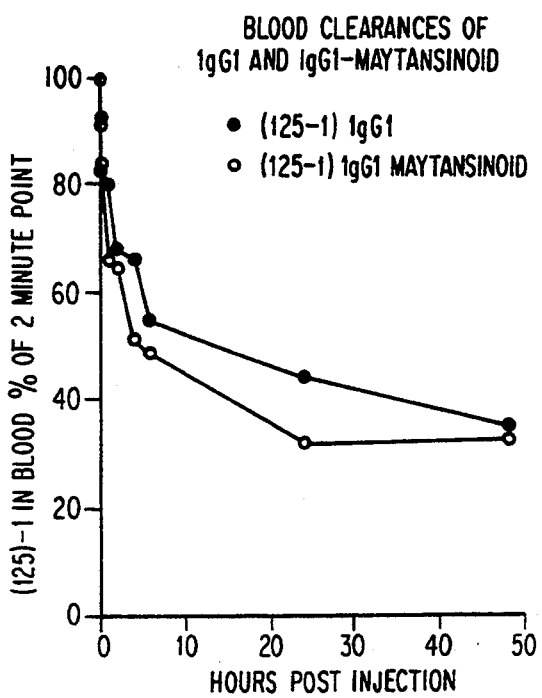
FIG. 7 shows graphically the blood clearance of an antibody-maytansinoid conjugate in mice.

Blood clearances of a typical $^{125}$I-labelled murine IgG$_1$ antibody and of its corresponding $^{125}$I-labelled maytansinoid conjugate, containing an average of 4 drug molecules/antibody molecule, were determined in female CD-1 mice. The antibody and the maytansinoid conjugates had been radioiodinated by the method of Bolton and Hunter (133 *Biochem. J.* 529–539 (1973)). Greater than 99% of the radioactivity in the samples was bound to protein. The antibody and conjugates (2.7×10$^5$ cpm each) were injected separately i.v. into the tail vein. Heparinized blood samples were collected from the retroorbital venus plexus at the indicated times and measured for radioactivity content. The results are summarized in FIG. 7. The antibody and its maytansinoid conjugate display very similar biphasic clearance profiles.

While the invention has been described in detail and with reference to specific embodiments thereof, it will be apparent to one skilled in the art that various changes and modifications can be made therein without departing from the spirit and scope of the invention.

What is claimed is:

1. A cytotoxic agent comprising one or more maytansinoids linked to a hormone or growth factor via a linking group comprising a disulfide group.

2. The cytotoxic agent of claim 1, wherein the maytansinoid is a maytansinoid ester.

3. The cytotoxic agent of claim 2, wherein the maytansinoid ester is a C-3 maytansinoid ester.

4. The cytotoxic agent of claim 3, wherein the maytansinoid ester is an N-methyl-alanine-containing maytansinoid ester.

5. The cytotoxic agent of claim 4, wherein the N-methyl-alanine-containing maytansinoid ester is represented by formula (I):

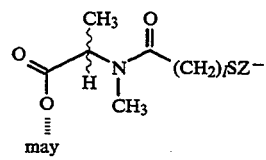

wherein:
l represents an integer of 1 to 10; and
may represents a maytansinoid.

6. The cytotoxic agent of claim 4, wherein the N-methyl-alanine-containing maytansinoid ester is represented by formula (II):

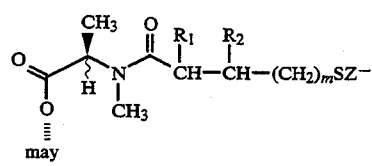

wherein:
R$_1$ and R$_2$, which may be the same or different, represents H, CH$_3$ or CH$_2$CH$_3$;
m represents 0, 1, 2 or 3; and
may represents a maytansinoid.

7. A cytotoxic agent of claim 4, wherein the N-methyl-alanine-containing maytansinoid ester is represented by formula (III):

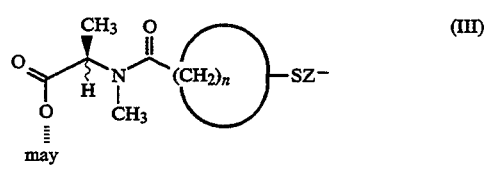

wherein:
n represents an integer of 3 to 8; and
may represents a maytansinoid.

8. The cytotoxic agent of claim 4, wherein the N-methyl-alanine-containing maytansinoid ester is a C-3 ester of maytansinol.

9. The cytotoxic agent of claim 8, wherein the maytansinoid ester is an ester of dechloro maytansinol.

10. The cytotoxic agent of claim 8, wherein the C-3 ester of maytansinol is represented by formula (IV):

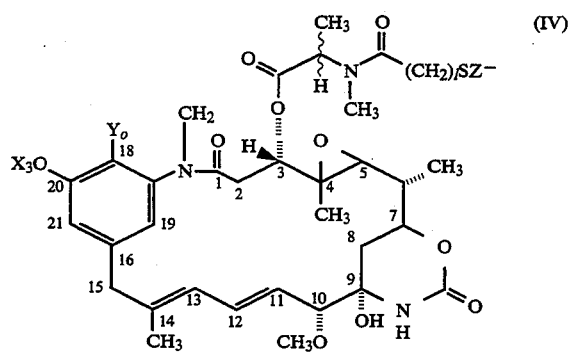

wherein:
l represents 1, 2 or 3;
Y$_0$ represents Cl or H; and
X$_3$ represents H or CH$_3$.

11. The cytotoxic agent of claim 8, which comprises N-methyl-N-(3-methyldithiopropanoyl)-L-alanine.

12. The cytotoxic agent of claim 3, wherein the maytansinoid ester is an N-methyl-cysteine-containing maytansinoid ester.

13. The cytotoxic agent of claim 12, wherein the N-methyl-cysteine-containing maytansinoid ester is represented by formula (V):

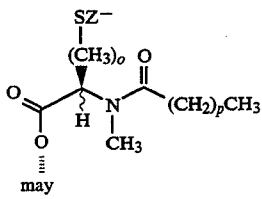

wherein:
o represents 1, 2 or 3;
p represents O or an integer of 1 to 10; and
may represents a maytansinoid.

14. The cytotoxic agent of claim 12, wherein the N-methyl-cysteine-containing ester is a C-3 ester of maytansinol.

15. The cytotoxic agent of claim 14, wherein the maytansinoid ester is an ester of dechloro maytansinol.

16. The cytotoxic agent of claim 12, wherein the N-methyl-cysteine-containing maytansinoid ester is represented by formula (VI):

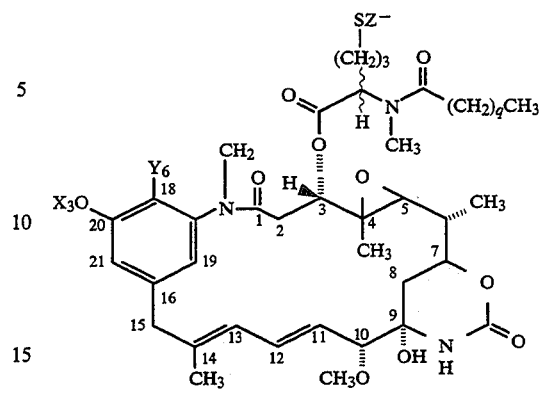

wherein:
o represents 1, 2, or 3;
q represents O or an integer of 1 to 10;
$Y_0$ represents Cl or H; and
$X_3$ represents H or $CH_3$.

17. The cytotoxic agent of claim 1, wherein said hormone is melanocyte stimulating hormone (MSH) or an analogue thereof.

18. The cytotoxic agent of claim 1, wherein said hormone is thyroid stimulating hormone (TSH) or an analogue thereof.

19. The cytotoxic agent of claim 1, wherein said growth factor is epidermal growth factor (EGF).

20. The cytotoxic agent of claim 1, wherein said growth factor is transforming growth factor alpha (TGF-α).

* * * * *